US008637230B2

(12) United States Patent
Doorschodt et al.

(10) Patent No.: US 8,637,230 B2
(45) Date of Patent: Jan. 28, 2014

(54) COMPOSITION FOR COLD PRESERVATION AND PERFUSION OF ORGANS

(75) Inventors: Benedict Marie Doorschodt, Amsterdam (NL); Maud Bessems, Amsterdam (NL)

(73) Assignee: Organoflush B.V., Amsterdam Zuidoost (NL)

( * ) Notice: Subject to any disclaimer, the term of this patent is extended or adjusted under 35 U.S.C. 154(b) by 1517 days.

(21) Appl. No.: 11/719,185

(22) PCT Filed: Nov. 11, 2005

(86) PCT No.: PCT/NL2005/050036
§ 371 (c)(1),
(2), (4) Date: Aug. 28, 2007

(87) PCT Pub. No.: WO2006/052133
PCT Pub. Date: May 18, 2006

(65) Prior Publication Data
US 2008/0187901 A1  Aug. 7, 2008

(30) Foreign Application Priority Data

Nov. 12, 2004  (EP) .................................. 04078113

(51) Int. Cl.
*A01N 1/00* (2006.01)
(52) U.S. Cl.
USPC ............................................ 435/1.1; 435/1.2
(58) Field of Classification Search
None
See application file for complete search history.

(56) References Cited

U.S. PATENT DOCUMENTS

| 4,784,852 A | 11/1988 | Johansson et al. |
| 4,938,961 A | 7/1990 | Collins et al. |
| 5,599,659 A | 2/1997 | Brasile et al. |
| 5,843,024 A | 12/1998 | Brasile |
| 6,641,992 B2 | 11/2003 | Lopez et al. |
| 2003/0129173 A1* | 7/2003 | Al-Abdullah et al. ..... 424/93.21 |

FOREIGN PATENT DOCUMENTS

| WO | WO 02/35929 A | 5/2002 |
| WO | WO 02/41696 A1 | 5/2002 |

OTHER PUBLICATIONS

Inoue et al., "CChanges of serum Vitamin A, vitamin E, selenium, lipid composition and blood glutathinoe peroxidase activity during the growth stage of Holstein bull calves and heifer calves", Nippon Juishikai Zasshi 44(9) : 887-92 (1991), abstract only.*
Hu et al., "The anitoxidan and prooxidant activity of some B vitamins and vitamin-like compounds", Chemico-Biological interactions 97 (1) : 63-73 (1995), abstract only.*
Gibco Catalog, Williams' Media E, p. 55, 1992.*
Wusteman, "Comparison of colloids for use in isolated normothermic perfusion of rabbit kidnyes", J. Surgical Research 25 (1) : 54-60 (1978), abstract only.*
Invitrogen Catalog, http://www.invitrogen.com/site/us/en/home/support/Product-Technical-Resources/media_formulation.7.html, 2 pages, accessed Jul. 6, 2011.*
Cho et al., "The study of cold preservation of rat cultured hepatocytes", Korus'99, Proceeding of the Russian-Korean International Symposium on Science and Technology, 3rd, Movosibirsk, Russian Federation, Jun. 22-25, vol. 2: 441-443 (1999), abstract only.*
ATCC Catalog, http://www.atcc.org/attachments/6661.pdf, 1 page, accessed Jul. 6, 2011.*
Darkwa et al., "Antioxidant Chemistry. Reactivity and oxidation of DL-cysteine by some common oxidants", J. Chem. Soc., Faraday Transactions 94 (14) : 1971-1978 (1998), abstract only.*
Adam, R. et al., "Effect of extended cold ischaemia with UW solution on graft function after liver transplantation", *The Lancet*, vol. 340, pp. 1373-1376, 1992.
Adham, M. et al., "The isolated perfused porcine liver: assessment of viability during and after six hours of perfusion", *Transpl. Int.*, vol. 10, pp. 299-311, 1997.
Athreya, B.H. et al., "Preservation of functioning rabbit hearts invitro preliminary communication on a new approach perfusion electrolytes nutrients tissue culture media inst. Electro cardiography", *Archives of Surgery*, vol. 97, No. 6, pp. 947-953, 1968.
Baicu, S.C. et al., "Acid-base buffering in organ preservation solutions as a function of temperature: New parameters for comparing buffer capacity and efficiency.", *Cryobiology*, vol. 45, pp. 33-48, 2002.
Bergmeyer, H.U., "Standardization of enzyme assays", *Clin. Chem.*, vol. 18, No. 11, pp. 1305-1311, 1972.

(Continued)

*Primary Examiner* — Sandra Saucier
(74) *Attorney, Agent, or Firm* — Gilberto M. Villacorta; Sunit Talapatra; Foley & Lardner LLP

(57) ABSTRACT

The current invention provides a new organ preservation solution, suitable for machine perfusion, for maintaining viability of organs, parts of organs and tissues. This solution has been designed to overcome a number of problems associated with hypothermic machine perfusion of donor organs, in particular organs obtained from non-heart-beating donors. The solution prevents or minimizes the adverse affects caused by ischemia, hypoxia, energy and nutrient depletion, acidification, hypothermia and reperfusion injury. The preservation solutions according to the current invention are superior to current state of the art preservation solutions, in particular for preservation and perfusion of organs obtained from non-heart-bearing donors, by supplying increased concentrations and an optimized balance of amino acids, vitamins, anti-oxidants, high molecular weight additives and enhanced buffering capacity. In addition, the preservation solution according to the invention combines optimal physical and chemical properties with the use of readily available, inexpensive and pharmaceutically tested and acceptable compounds, reducing the cost of manufacturing and facilitating medical certification of solutions according to the current invention.

20 Claims, 12 Drawing Sheets

(56) References Cited

OTHER PUBLICATIONS

Figure 1:
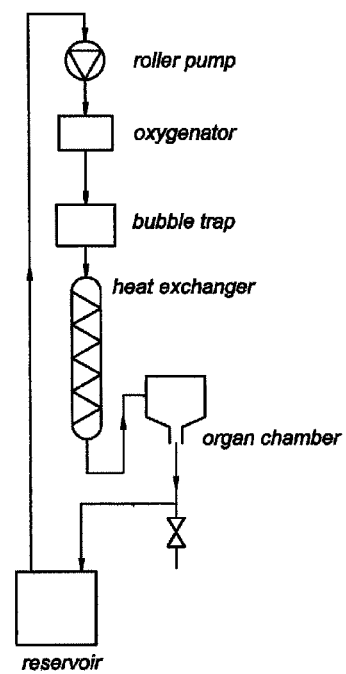

Bessems, M. et al., "Improved rat liver preservation by hypothermic continuous machine perfusion using Polysol, a new, enriched preservation solution.", *Liver Transpl.*, vol. 11, No. 5, pp. 539-546, 2005.
Boudjema, K. et al., "Effects of method of preservation on functions of lives from fed and fasted rabbits", *Cryobiology*, vol. 28, pp. 227-236, 1991.
Charrueau, C. et al., "Prevention of proteolysis in cold-stored rat liver by addition of amino acids to the preservation solution", *J. Gastroenterol Hepatol.*, vol. 15, pp. 1199-1204, 2000.
Churchill, T.A. et al., "Protective properties of amino acids in liver preservation: effects of glycine and a combination of amino acids on anaerobic metabolism and energetics", *J. Hepatol.*, vol. 23, pp. 720-726, 1995.
Churchill, T.A. et al., "Investigation of a primary requirement of organ preservation solutions: Supplemental buffering agents improve hepatic energy production during cold storage", *Transplantation (Baltimore)*, vol. 65, No. 4, pp. 551-559, 1998.
Compagon, P. et al., "Effects of hypothermic machine perfusion on rat liver function depending on the route of perfusion", *Transplantation*, vol. 72, No. 4, pp. 606-614, 2001.
Crocker, C.L., "Rapid determination of urea nitrogen in serum or plasma without deproteinization", *Am. J. Med. Technol.*, vol. 33, No. 5, pp. 361-365, 1967.
Fonseca-Wollheim, F., "[Direct determination of plasma ammonia without doproteinization. An improved enzyme determination of ammonia, II (author's translation)]", *Z. Klin. Chem. Klin. Biochem.*, vol. 11, pp. 426-431, 1973.
Fukumori, T. et al., "Use of older controlled non-heart-beating donors for liver transplantation", *Transplantation*, vol. 75, No. 8, pp. 1171-1174, 2003.
Gridelli, B. et al., "Split-liver transplantation eliminates the need for living-donor liver transplantation in children with end-stage cholestatic liver disease", *Transplantation*, vol. 75, No. 8, pp. 1197-1203, 2003.
Husberg, B., "Prolonged In-Vivo Perfusion of Rabbit Kidneys with N-2 Di Hydroxyethyl Piperazine-N-Ethane Sulfonic-Acid", *European Surgical Research*, vol. 3, No. 6, pp. 402-408, 1971.
Janβen et al., "Celsior solution compared with University of Wisconsin solution (UW) and histidine—tryptophan—ketoglutarate solution (HTK) in the protection of human hepatocytes against ischemia—reperfusion injury", *Transplant International*, vol. 16, No. 7, pp. 515-522, 2003.
Kim, J.S. et al., "Machine perfusion of the liver: maintenance of mitochondrial function after 48-hour preservation", *Transplant Proc.*, vol. 29, pp. 3452-3454, 1997.
Lee, D. et al., "Maintenance of functional state of isolated rat liver by hypothermic perfusion with an erythrocyte-free medium", *Transplantation*, vol. 23, No. 2, pp. 136-141, 1977.
Marsh, D.C. et al., "Hypothermic preservation of hepatocytes. I. Role of cell swelling", *Cryobiology*, vol. 26, pp. 524-534, 1989.
Marsh, D.C. et al., "Hypothermic preservation of hepatocytes. II. Importance of Ca2 and amino acids", *Cryobiology*, vol. 27, pp. 1-8, 1990.
Martin, H. et al., "Cryopreserved rat liver slices: a critical evaluation of cell viability, histological integrity, and drug-metabolizing enzymes", *Cryobiology*, vol. 41, pp. 135-144, 2000.
Morariu, A.M. et al., "Hyperaggregating effect of hydroxyethyl starch components and University of Wisconsin solution on human red blood cells: a risk of impaired graft perfusion in oran procurement?", *Trnasplantation*, vol. 76, No. 1, pp. 37-43, 2003.
Neuberger, J.M. et al., "Living-related liver donation: the inevitable donor deaths highlighted the need for greater transparency", *Transplantation*, vol. 77, No. 4, pp. 489-490, 2004.
Neuhaus, P. et al., "[Indications and current developments in liver transplantation]", vol. 19, pp. 289-308, 1989.
Nunez, A. et al., "Enlargement of the cadaveric-liver donor pool using in-situ split-liver transplantation despite complex hepatic arterial anatomy", *Transplantation*, vol. 76, No. 7, pp. 1134-1136, 2003.
Oh, C.K. et al., "Implication of advanced donor age on the outcome of liver transplantation", *Clin. Transplant*, vol. 14, pp. 386-390, 2000.
Pienaar, B.H. et al., "Seventy-two-hour preservation of the canine liver by machine perfusion", *Transplantation*, vol. 49, No. 2, pp. 258-260, 1990.
Porte, R.J. et al., "Long-term graft survival after liver transplantation in the UW era: late effects of cold ischemia and primary dysfunction", European Multicentre Study Group, *Transpl. Int.*, vol. 11, Supl. 1:, pp. S164-S167, 1998.
Ringe, B. et al., "Quadrennial review on liver transplantation", *Am. J. Gastroenterol*, vol. 89, No. 8, pp. S18-S26, 1994.
Rubinsky, B., "Principles of low temperature cell preservation", *Heart Failure Reviews*, vol. 8, pp. 277-284, 2003.
Schon, M.R. et al., "The possibility of resuscitating livers after warm ischemic injury", *Transplantation*, vol. 56, No. 1, pp. 24-31, 1993.
Southard, J.H., et al., Kupffer cell activation in liver preservation: cold storage vs machine perfusion, *Transplant Proc.*, vol. 32, pp. 27-28, 2000.
St. Peter, S.D. et al., "Liver and kidney preservation by perfusion", *Lancet*, vol. 359, pp. 604-613, 2002.
Tojimbara T. et al., "Liver transplantation from non-heart beating donors in rats: influence of viscosity and temperature of initial flushing solutions on graft function", *Liver Transpl. Surg.*, vol. 3, No. 1, pp. 39-45, 1997.
Turner, M.D. et al., "Successful 20-hour storage of the canine liver by continuous hypothermic perfusion", *Cryobiology*, vol. 6, No. 4, pp. 293-301, 1970.
Uchiyama, M. et al., "Usefulness of preservation by machine perfusion of liver grafts from non-heart-beating donors—a porcine model," *Transplant. Proc.*, vol. 35, pp. 105-106, 2003.
Van Slyke, D. "On the measurement of buffer values and on the relationship of buffer value to the dis-sociation constant of the buffer and the concentration and reaction of the buffer solution", *The Journal of Biological Chem.*, vol. 52, pp. 525-570, 1922.
Verran, D. et al., "Clinical experience gained from the use of 120 steatotic donor livers for orthotopic liver transplantation", *Liver Transpl*, vol. 9, pp. 500-505, 2003.
Williamson, J.R. et al., "Assay of citric acid cycle intermediates and related compounds—update with tissue metabolite levels and intracellular distribution", *Methods Enzymol*, vol. 55, pp. 200-222, 1979.
Xu, H. et al., "Pronlonged hypothermic machine perfusion preserves hepatocellular function but potentiates endothelial cell dysfunction in rat livers", *Transplantation*, vol. 77, No. 2, pp. 1676-1682, 2004.
Otte, "Donor Complications and Outcomes in Live-Liver Transplantation," *Transplantation*, vol. 75, No. 10, May 27, 2003, pp. 1625-1626.
Bessems et al., "Improved machine perfusion preservation of the non-heart-beating donor rat liver using Polysol: a new machine perfusion preservation solution," Liver Transplantation, 2005, vol. 11, No. 11, pp. 1379-1388.
Bessems et al., "Machine perfusion preservation of the non-heart-beating donor rat livers using Polysol: a new preservation solution," Transplantation Proceedings, 2005, vol. 37, pp. 326-328.
Bessems et al., "Optimization of a new preservation solution for machine perfusion of the liver: which is the preferred colloid?" Transplantation Proceedings, 2005, 37, pp. 329-331.
International Search Report for PCT/NL2005/050036, dated Jun. 23, 2006, 4 pages.
Schreinemachers et al., "Pulsatile perfusion preservation of warm ischaemia-damaged experimental kidney grafts," British Journal of Surgery, 2010, vol. 97, pp. 349-358, John Wiley & Sons Ltd.

\* cited by examiner

COMPOSITION FOR COLD PRESERVATION AND PERFUSION OF ORGANS

FIELD OF THE INVENTION

The current invention relates to the fields of medicine and in particular to transplantation of solid organs and tissues. The present invention provides a novel solution and method for preserving donor organs and tissues from humans and animals, in particular liver and kidney, for perfusion and at low temperatures.

BACKGROUND OF THE INVENTION

Organ transplantation is currently widely applied for organs such as heart, lung, pancreas, intestine (colon) and in particular kidney and liver. Increased organ demand and a shortage of donor organs has led to an increased waiting list for transplantation and a resulting interest in use of organs from sub-optimal donors.

Preservation of viability of donor organs is an important aspect in transplantation procedures. Organs to be transplanted obtained from cadavers must be stored and transported between hospitals and/or transplantation centers. Time is required for histo-compatibility testing of donor and recipient, and for the preparation of the receiving patient. Between retrieval from a donor and transplantation to a recipient, organs require special methods of preservation. The length of time that organs and tissues can be kept outside the body varies, depending on the organ, age and health of donor, the preservation method, preservation solution and temperature.

The standard clinical practice to date for preservation of most donor organs is hypothermic ischemic preservation. Organs are harvested from cadaveric donors after wash-out with a cold preservation solution. Thereby organs are exsanguinated and blood is replaced by a preservation solution which preferably mimicks physiological conditions. To replace blood and oxygen support of the organ and to maintain the organ in optimal condition, machine perfusion with a hypothermic preservation solution is sometimes applied for organs such as kidneys (WO 02/41696, U.S. Pat. No. 5,599,659 and U.S. Pat. No. 5,843,024). Machine perfusion allows the supply of compounds and oxygen to maintain organ viability, as well as removal of waste and toxic compounds, such as metabolites. Machine perfusion has shown to be superior to static preservation, although it has several possible drawbacks such as requirements for specialized equipment and trained personnel and additional requirements for the preservation solution applied.

The most commonly used solutions for donor organ preservation at hypothermic, static conditions are the University of Wisconsin solution (UW), in particular for liver and kidney (Janssen et al, Transplant International 2003, vol 16, no 7, p 515-522), Celsior for heart preservation and Euro-Collins or Perfadex for lung preservation. For machine perfusion, these have been modified to for instance UW-gluconate (Belzer MPS).

The current invention provides a new organ preservation solution, suitable for machine perfusion, for maintaining viability of organs, parts of organs and tissues. This solution has been designed to overcome a number of problems associated with hypothermic machine perfusion of donor organs, in particular organs obtained from sub-optimal donors, in particular non heart beating donors. The solution prevents or minimizes the adverse affects caused by ischemia, hypoxia, energy and nutrient depletion, acidification, hypothermia and reperfusion damage, which is experienced by organs to be used for transplantation purposes, and in particular by organs obtained from sub-optimal donors. The preservation solutions according to the current invention are superior to current state of the art preservation solutions, and are in particular advantageous for preservation and perfusion of organs obtained from sub-optimal donors, by supplying increased concentrations and an optimized balance of amino acids, vitamins, anti-oxidants, high molecular weight additives and enhanced buffering capacity. In addition, the preservation solution according to the invention combines optimal physical and chemical properties with the use of readily available, inexpensive and pharmaceutically tested and acceptable compounds, which reduces the cost of manufacturing and will facilitate medical certification of solutions according to the current invention.

DETAILED DESCRIPTION

Definitions

Normothermia is the body, organ and/or tissue temperature under normal physiological circumstances, roughly between 34° C. and 42° C. for humans, preferably around 37° C. Hypothermia is a lower than physiological temperature, i.e. lower than 34° C. For organ preservation 0-20° C., in particular 0-10° C. is considered hypothermia.

Ischemia is an insufficient supply of oxygen to a limb, organ or tissue, usually due to a blocked blood flow by occlusion of an artery, but also after removal of an organ from a donor, resulting in, amongst others, a decreased oxygen pressure, i.e. a $pO_2$ lower than physiologically sustainable levels, which will result in damage of the tissues of the organ or limb.

Perfusion: constant or pulsatile flow of blood or within the scope of the current invention a blood replacing artificial organ preservation and perfusion solution through or around an organ, part thereof or tissue, preferably through the vasculature.

Sub-optimal donor and organ obtained from a sub-optimal donor: an organ from a donor in sub-optimal condition, for instance a non-heart-beating donor, a steatotic liver donor or an elderly donor. In the non-heart-beating donor the heart has been irreversibly arrested for a minimum period of 10 minutes (at normothermia) and whereby death has been confirmed by a physician. A steatotic liver is a liver which consists of more than 30% steatotic hepatocytes, i.e. an accumulation of fatty acids in the hepatocytes (occurring in 30% of all potential donors). A donor aged over 60 is considered an elderly donor, although this age limit may be stretched to even 70 years or more.

The expression "organs, tissues and parts thereof" in this application comprise all parts of a mammalian body which can be transplanted at present time or in the future.

The expression "physiological concentration" or "physiological value" of a certain parameter such as osmolarity, temperature, oncotic pressure etc, used throughout the specification, means a concentration which mimicks the physiological value of this parameter in the mammalian body under physiological circumstances of the mammal in good health.

Osmolarity is a measure of the osmotic pressure exerted by a solution across a perfect semi-permeable membrane (one which allows free passage of water and completely prevents movement of solute) compared to pure water. Osmolarity is dependent on the number of particles in solution but independent of the nature of the particles.

Oncotic pressure: In blood plasma the dissolved compounds yield an osmotic pressure. A small portion of the total osmotic pressure is due to the presence of large protein molecules; this is known as the colloidal osmotic pressure, or oncotic pressure. Because large plasma proteins cannot easily cross through the capillary walls, their effect on the osmotic pressure of the capillary interiors will, to some extent, balance out the tendency for fluid to leak out of the capillaries. In conditions where plasma proteins are reduced, e.g. from being lost in the urine (proteinuria) or from malnutrition, or in the case of organs taken out of a body for transplantation and stored in a fluid, the result of the low oncotic pressure can be edema—excess fluid build-up in the tissues. Oncotic pressure is expressed in mmHg (millimeters of mercury pressure).

Because the capillary wall is permeable to water, but essentially impermeant to the larger plasma proteins, these molecules generate an osmotic pressure. Furthermore, since these proteins are negatively charged, they tend to hold additional cations in the plasma (the Gibbs-Donnan effect), further enhancing an osmotic gradient between the plasma and the interstitial fluid (ISF). The combined effect (osmotic and Gibbs-Donnan) results in a pressure that draws water out of the interstitium and into the plasma. This pressure is defined as the Colloid Oncotic Pressure (often shortened to the Oncotic Pressure). This pressure is proportional to the difference in protein concentration between the plasma and the ISF. Compared to pure saline, the human plasma exerts about 28 mm Hg Oncotic pressure, whereas the ISF has only about 3 mm Hg. The net Oncotic Pressure is thus about 25 mm Hg. This value remains roughly constant over the length of most capillary beds.

A buffer herein is defined as "a substance which by its presence in solution increases the amount of acid or alkali that must be added to cause unit change in pH". Buffers are thus very important components in organ preservation and perfusion solutions, by maintaining a constant concentration of hydrogen ions within the physiological range. The pH of mammalian blood is maintained close to 7.38 by buffer systems such as:

$$H_2PO_4^- <=> HPO_4^{2-}, CO_2 <=> H_2CO_3,$$

$$H_2CO_3 <=> HCO_3^-,$$

many organic acids, organic bases and proteins. Universally applicable and biologically acceptable buffers for the solution according to the current invention must display: water solubility, no interference with biological processes or known complex-forming tendency with metal ions, non-toxicity and no interference with biological membranes (such as penetration, solubilisation, adsorption on surface).

The buffer capacity is influenced by temperature and other solutes in the composition. Activity and salt effects have a marked influence on the pH value of a solution according to the equation $$pH = pKa' + \log [B]/[BH] \quad (1)$$

where $pKa' = pKa + $ correction factor

Ionic strength of a solution is defined as in $$I = \tfrac{1}{2}\Sigma(c_i z^2)$$

where $c_i$ is the concentration of species i, and z is the corresponding charge. It can be calculated very easily from the experimental parameters.

Buffer Capacity is the ratio of the increment of strong base or strong acid to the change in pH.

$$B = \Delta B/\Delta pH$$

= the small increment in gram equivalents/liter of strong base (or acid) added to buffer solution to produce a pH change of $\Delta pH$.

$$B = (2.3 \times C \times K_a[H^+])/(K_a + [H^+])^2$$

$$B = 2.3Ca(1-a)$$

$$C = [Acid] + [Salt]$$

or $$C = [Base] + [Salt]$$

The maximum buffer capacity Beta-max of a monovalent species is found to be at pH=pKa', the practical pK-value. Beta max in the pH range 3-11 is calculated according to equation:

beta max=0.576c where c is the total concentration of the buffer substance.

Thus a useful buffer capacity lies within a pH range of pKa±1 unit. If more than 50% of the maximum buffer capacity must be realized, the corresponding range is only pKa'+ 0.75 units.

The buffer capacity of a solution can also be expressed in Slykes units. Buffering capacity, measured in slykes, is defined as the mmoles of base required to titrate the pH of 1 g wet mass of muscle/tissue by 1 pH unit, over the pH range 6 to 7 (Van Slyke, Biol. Chem. 52, 525-570, 1922). For this application the Beta is defined as the μmoles of sodium hydroxide or hydrogen chloride required to change the pH of one gram of tissue by one unit, i.e., from 6 to 7 or from 6.5 to 7.5.

Tissue culture media comprise fluids which can sustain the growth and preservation of mammalian cells in in vitro culture, comprising of biologically acceptable buffers, salts, nutrients such as a carbon source, amino acids, nutrients, vitamins, mimicking physiological conditions in the body regarding pH, osmolarity and oncotic pressure. Examples of standard tissue culture media used in the art and readily commercially available comprise at least the following non-exhaustive list of widely used media: Minimal Essential Medium Eagle (MEM), Dulbecco's Modified Eagle Media (DMEM), RPMI 1640 Media, DMEM/F-12 Media, Hams F-10, Hams F12, Iscove's Modified Dulbecco's Medium, Leibovitz's L-15 Media and Minimum Essential media with Earle's Salts and Williams E medium.

Embodiments

In a first embodiment the present invention provides an organ preservation and perfusion solution based on tissue culture media, to provide a sufficient amount of vitamins and nutrients to the organ in a well balanced way. Many tissue culture media are known in the art and are well documented and commercially available from various suppliers. Minimal Essential Medium Eagle (MEM), Dulbecco's Modified Eagle Media (DMEM), RPMI 1640 Media, DMEM/F-12 Media, Hams F-10, Hams F12, Iscove's Modified Dulbecco's Medium, Leibovitz's L-15 Media and Minimum Essential media with Earle's Salts and Williams E media (Current Protocols in cell biology, www.interscience.wiley.com) may be used as a basis for the organ preservation solution according to the current invention, but also other cell or tissue culture media known in the art may be used. In particular, Williams E is well suited and preferred for an organ preservation and perfusion solution according to the current invention. Tissue culture media comprise physiological salts and buffering compounds, keeping the osmolarity and pH at physiological conditions, i.e. around 300-350 mOsmol and a pH range of pH 7.0 to pH 7.8. Also nutrients, (sugars, vitamins, amino acids) are provided for in most defined and undefined tissue culture media. The current inventors have found that in order to optimize a tissue culture medium for use as an organ preservation solution, suitable for both preservation and perfusion of organs at low temperatures, several adjustments and additions should be made to the solution. These adjustments have proven to be particularly useful for preservation and perfusion of organs obtained from normally less preferred, sub-optimal donors.

An organ preservation and perfusion solution according to the current invention is optimized for and preferably used at lower than physiological temperatures, ranging from around 0° C. to around 20° C., preferably between 4° C. and 10° C. Organs stored at relatively low temperatures have a reduced requirement for oxygen and nutrients, as the metabolism at 18° C. is only 10 to 15% of the metabolic rate at physiological temperatures around 37° C. However, the inventors have found that even at a relatively low metabolic activity, nutrients such as glucose, amino acids and vitamins are still utilized and should be provided in sufficient quantities. The inventors have found that increasing the dosage/concentration of amino acids and other nutrients will facilitate a sufficient cellular uptake even at low temperatures and under decreased perfusion or flow conditions outside the body in an artificial medium, such as a preservation and perfusion solution according to the current invention. The increased concentration of amino acids and vitamins has proven to be particularly useful for the preservation of organs obtained from non-heart-beating donors. In a preferred embodiment, the concentration of the following group of amino acids is increased relative to the standard amino acid concentrations in Williams E Media: arginine, asparagine, cystine, histidine, glutamine, methionine, phenylalanine, proline, serine and tryptophan. An highly optimized, but non limiting example of a solution according the invention, is given in comparative example 1.

An organ preservation and perfusion solution according to the current invention also has a specific and optimized balance of $[Na^+]$ to $[K^+]$ concentrations. Under normal physiological circumstances the intracellular concentration of $[K^+]$ is significantly higher than the intracellular concentration of $[Na^+]$, whereas the situation in the interstitial lumen is the reverse. The organ preservation and perfusion solution according to the current invention is designed to mimick the physiological extracellular concentration, in order to facilitate the organ, tissues and cells to maintain a physiological $[Na^+]/[K^+]$ balance which is required for driving, among others, the ionic transport conducted by sodium pumps. The imbalance in intracellular and extracellular $[Na^+]$ on $[K^+]$ concentrations creates both an electrical and chemical gradient across the plasma membrane. This is critical not only for the cell but, in many cases, for directional fluid and electrolyte movement across epithelial sheets. The $Na^+$—$K^+$-ATP-ase is a highly-conserved integral membrane protein that is expressed in virtually all cells of higher organisms. It provides the driving force for several facilitated transporters, which import glucose, amino acids and other nutrients into the cell. This transport has proven to be critical for low temperature preservation and perfusion of organs, in particular for organs from non-heart-beating donors, by the experiments performed by the current inventors. Translocation of sodium from one side of an epithelium to the other side creates an osmotic gradient that drives absorption of water. Important instances of this phenomenon can be found in the absorption of water, for instance from the lumen of the small intestine and in the kidney. Therefore it is important that the composition according to the current invention mimicks the physiological extracellular $[Na^+]/[K^+]$ balance of at least 2:1, more preferably 3:1 and most preferably 5:1.

A highly preferred additive in the organ preservation and perfusion solution according to the current invention is a high molecular weight compound to provide the required oncotic pressure. Several high molecular weight additives that can be advantageously used in organ preservation and perfusion solutions are known in the art, such as polyethylene glycols (PEG) and modifications thereof (U.S. Pat. No. 4,938,961 and U.S. Pat. No. 5,599,659), dextrans, serum proteins such as albumins, hydroxyethylstarch (HES), and other high molecular weight sugars and biocompatible polymers of net negative charge in pH neutral solutions. Because large plasma proteins cannot easily cross through the capillary walls, their effect on the osmotic pressure of the capillary interiors will, to some extent, balance out the tendency for fluid to leak out of the capillaries. In conditions where plasma proteins are reduced, e.g. for instance in case of organs taken out of a body for transplantation purposes and stored in a preservation fluid, the result of the too low oncotic pressure is edema—excess fluid buildup in the tissues. This problem needs to be addressed, in particular for organs obtained from non-heart-beating donors which often are in a slightly deteriorated condition. Therefore, negatively charged high molecular weight molecules are added, to maintain a physiological oncotic pressure, which is expressed in mm Hg (millimeters of mercury pressure). Preferably the organ preservation and perfusion solution of the current invention yields an oncotic pressure of 20 to 30 mmHg, preferably around physiological levels, close to 25 mmHg. In a preferred embodiment, PEG is used as a high molecular weight additive in organ preservation solutions of the current invention. In a most preferred embodiment PEG of a molecular weight of 25,000 to 50,000 daltons is used, preferably at concentrations in the range of 10 to 50 grams per Liter, most preferably between 20 and 35 grains per Liter. However, other high molecular weight compounds such as HES, albumins and dextrans may be advantageously used for generating oncotic pressure, optionally in combination with PEGs.

Control of pH and prevention of intracellular pH increase are critical properties of organ preservation and perfusion solutions. Ischemia, hypoxia, energy depletion and hypothermia are factors known to result in a drop of pH levels and may lead to acidification of cells, tissues and organs to be transplanted. Acidity is a widely recognized hazard for cells and tissues and will quickly deteriorate the condition of the organ to be transplanted (Baicu and Taylor, 2002 Cryobiology 45 p. 33-48). Acidity is in particular a problem that needs to be addressed for organs obtained from non-heart-beating donors, which already experienced ischemia, hypoxia and depletion of nutrients. The preservation solutions according to the current invention are optimized to address and overcome these problems.

To prevent acidification of the organ stored at low temperature and with no or a decreased artificial perfusion, providing additional buffer capacity is another key feature of the organ preservation and perfusion solution according to the current invention. Although tissue culture media have a biologically acceptable buffer optimized for a physiological pH between pH 7.0 and pH 7.8, preferably around pH 7.4 at physiological temperatures of around 37° C., additional buffering capacity is required for the above mentioned reasons. An organ preservation and perfusion solution for low temperatures, between 0° C. and 20° C., according to the current invention is provided with a buffering system with a minimum capacity (Beta) of at least 20, more preferably 25, 30, 35, 40, 50, 100 to 250, and most preferably at least 30 to 35 as measured in Slykes units (slykes unit=(millimoles acid added per unit change to pH)). Buffering capacity (β) in slykes is defined as the number of millimoles of strong acid to change pH of 1 g of muscle or tissue by 1 pH unit over the range pH 7 to pH 6 (defined by van Slyke, JBC, 1922). The strong acid may be HCL, a strong base for changing pH from 6 to 7, NaOH may be used.

Biologically and physiologically acceptable buffers that have a suitable pKa range and may be advantageously used in solutions according to the current invention are selected from the group consisting of HEPES, PIPES, MOPS, TES, BES, Bicine, Tricine, Tris, Citrate, Histidine, $KH_2PO_4$, $K_2HPO_4$, $NaHCO_3$ and other phosphate-, citrate- and carbonate-buffers, known and well documented in the art (Current Protocols, Wiley Interscience, 2004). HEPES is the most preferred buffer in solutions according to the current invention to provide the desired (additional) buffer capacity, preferably at concentrations between 1000-10000 mg/L, most preferably between 2500 and 7500 mg/L.

The pH of the organ preservation may be adjusted using $Mg(OH)_2$, NaOH, KOH, $Ca(OH)_2$ or combinations thereof, to a final pH between 7 and 8, preferably around 7.5 at room temperature.

Oxygenation of the organ preservation solution with oxygen containing gas mixtures is highly preferred, both prior and during use for preservation and/or perfusion of an organ. Preferably gas mixtures with high or even pure oxygen may be used, to further aid in prevention of acidification of the organ preservation solution by $CO_2$ and other sources of acidification in the stored or perfused organ.

The organ preservation and perfusion solution according to the current invention preferably has a osmolarity between 300 and 400 mOsm, more preferably in the physiological range of 320 to 350 mOsm, most preferably around 340 mOsm.

In another preferred embodiment of the current invention, additional impermeants are added to the organ preservation and perfusion solution. Impermeants are substances of relatively high molecular weight that cannot, or only at a low rate, pass through membranes, and are added to increase the osmolarity without significantly altering the electrolytic composition of the solution, by for instance the addition of salts. Impermeants which may be used in the solution according to the current invention are selected from the group consisting of raffinose, trehalose, mannitol, sucrose, glucose, xylitol, lactobionate and gluconic acid (magnesium, potassium or sodium bound). In a preferred embodiment, raffinose and trehalose are used as impermeants, preferably at concentrations in the range of 1000 to 5000 mg/L, most preferably between 1200 and 2500 mg/L for trehalose and for raffinose, respectively. Gluconic acid is used preferably at concentrations in the range of 1000 to 5000 mg/L, most preferably between 1200 and 2500 mg/L.

In yet another preferred embodiment of the current invention, the organ preservation and perfusion solution comprises compounds capable of inhibiting or preventing the consequences of oxidative stress, in particular oxygen and other free radical activity. Reperfusion injuries in the organ commences with biochemical events during ischemia, which results in the formation of free oxygen radicals. Reperfusion injury is a problem for all transplantation organs in general, but in particular a considerable problem for organs obtained from non-heart-beating donors that have sustained damage from ischemia, hypoxia and nutrient depletion. Free radicals produced normally in the cell are removed by scavengers, compounds capable of neutralizing free radicals, and by enzymes, such as superoxide dismutase, glutathione peroxidase, tocopherol. Compounds limiting oxidative stress which are preferably added to the solution of the current invention comprise, but are not limited to: hypoxanthine, glutathione, allopurinol, trolox, vitamin E, methylene blue, ascorbic acid. Preferably glutathione, vitamin E and ascorbic acid are used in the solution according to the current invention, at concentrations preferably in the ranges of resp. 0.7-1.8 g/l for glutathione, 0.00001-0.001 for vitamin E and 0.01-0.1 g/L for ascorbic acid, respectively.

Selenium is an essential element involved primarily in enzymes that are antioxidants. Three selenium-containing enzymes are antioxidant peroxidases and a fourth selenium-containing enzyme is involved in thyroid hormone production. In combination with Vitamin E, selenium aids the production of antibodies and helps maintain a healthy heart. It also aids in the function of the pancreas, liver and kidneys, it provides elasticity to tissues and helps cells defend themselves against damage from oxidation. Vitamin E is an essential fat-soluble vitamin. As an antioxidant it helps to protect cell membranes, lipoproteins, fats and vitamin A from destructive oxidation. It also helps protect red blood cells and is important for the proper function of nerves and muscles. Selenium is an essential mineral which works closely with vitamin E. In a preferred embodiment of the organ preservation and perfusion solution of the current invention, a source of selenium is provided, to provide additional protection against oxidative stress and reperfusion injury. This has proven to be particularly advantageous for organs obtained from non-heart-beating donors and organs that have sustained ischemia and hypoxia. Toxicity is more of a problem with selenium than most nutrients, and the concentration of selenium is carefully adjusted in the range from 0.00001 to 0.001 g/l, preferably from 0.00003 to 0.0001 g/l. Organic and inorganic forms of selenium may have different properties. Organic forms include selenomethionine, selenocysteine, amino acid chelates and may be incorporated in a solution according to the current invention. Inorganic forms include sodium selenite and sodium selenate, which are the preferred source of selenium in the organ preservation and perfusion solution according to the current invention.

In a further aspect of the invention, there is provided a method for preserving, flushing and/or perfusing an organ, comprising the use of the preservation and perfusion solution as disclosed herein for the preservation of cells, tissues and organs in the absence of a blood supply, and to prevent or minimize damage to organs, living tissues and living cells during storage. The solutions are suited for the use of all transplantable mammalian organs comprising heart, lung, pancreas and intestine. In a most preferred embodiment the method for preserving an organ is directed at the cold perfusion and preservation of kidney and liver organs. The solution according to the current invention may be used in transplantation procedures for organs from heart-beating donors and in particular from sub-optimal donors. Preferably the preservation solution and the organ to be preserved are kept at a temperature within the range of 0° C. to 20° C., most preferably between 2° C. and 10° C.

Preferably the solution is used for continuous or pulsatile perfusion of the organ, most preferably by machine perfusion. Preferably the organ is perfused through the vascular system of the organ, using methods and equipment well known to those skilled in the art of organ transplantations, in particular of liver and kidney transplantations for humans.

Other advantages of the organ preservation method and the cold preservation and perfusion solution according to the current invention are the use of readily available, inexpensive and pharmaceutically tested and acceptable compounds, which reduces the cost of manufacturing and facilitates medical certification of solutions according to the current invention, and their use in the clinic.

FIGURE LEGENDS

FIG. 1: The double perfusion system for both 24 hours MP as well as for 60 minutes reperfusion. The system consists of a reservoir from which the perfusion solution is pumped by a roller pump through the glass oxygenator. After oxygenation and removal of air emboli, the solution is either cooled or heated in the heat exchanger. After passing a flow probe, the solution perfuses the liver via the portal vein canula and runs off freely via the caval vein into the perfusate reservoir. Before entering the reservoir, samples can be taken for assessment of liver damage and function.

Figure 2:
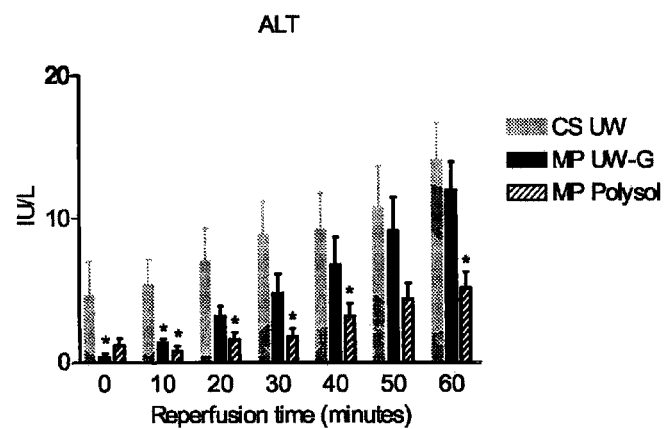

FIG. 2: Perfusate ALT levels during 60 minutes of normothermic reperfusion with KHB. Reduction in ALT is shown at all time points for MP vs CS. A reduction in ALT release in MP livers using POLYSOL vs CS in UW was found at t=10-20-30-40-60 minutes of RP and in MP livers using UW-G vs CS in UW at t=0-10 minutes of RP. Values (N=5) are expressed as mean±SEM.

Figure 3:
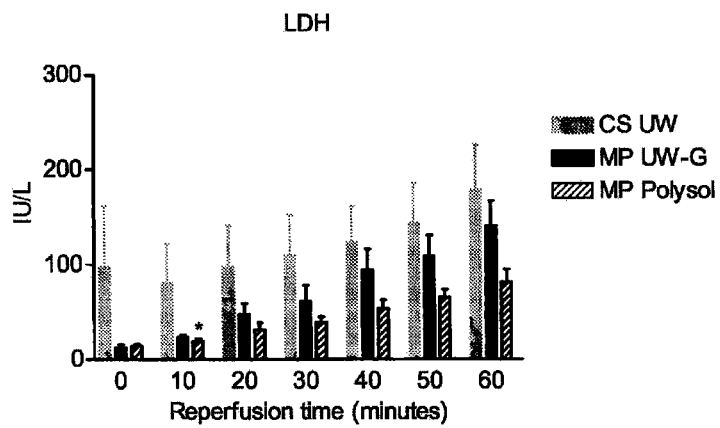

FIG. 3: Perfusate LDH levels during 60 minutes of normothermic reperfusion with KHB. Decreased LDH levels are shown for MP vs CS. Values for MP using POLYSOL vs CS in UW are lower at t=10 minutes of RP. Values (N=5) are expressed as mean±SEM.

Figure 4:
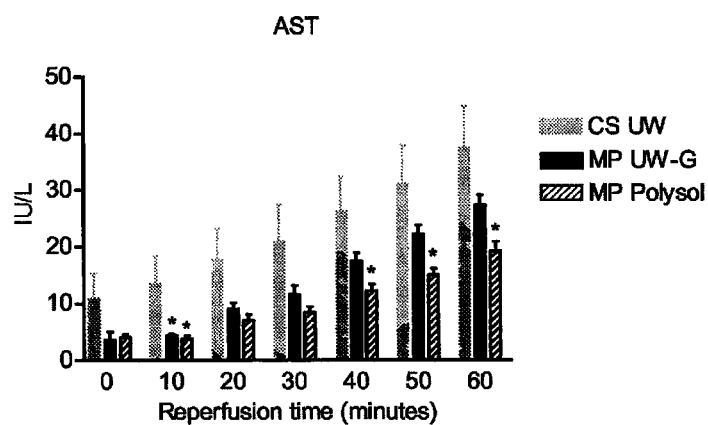

FIG. 4: Perfusate AST levels during 60 minutes of normothermic reperfusion with KHB. Decreased release of AST after 24 h MP vs CS in UW. Significant reduction of AST release after MP using UW-G vs CS in UW at t=10. Significantly decreased levels of AST are shown after MP using POLYSOL vs MP using UW-G at t=40-50-60 minutes of RP. Values (N=5) are expressed as mean±SEM.

Figure 5:
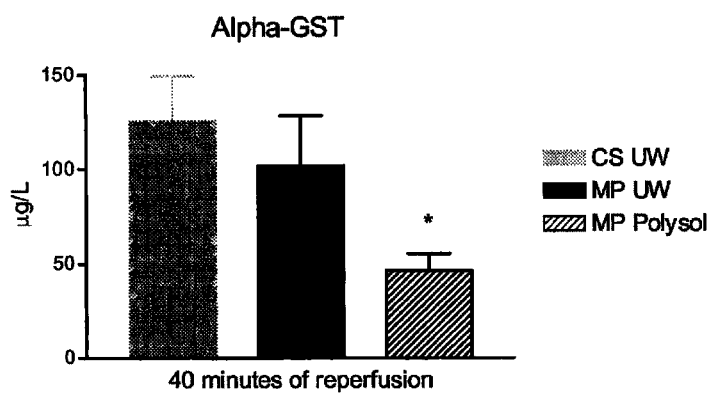

FIG. 5: Perfusate alpha-GST levels during 60 minutes of normothermic RP with KHB. A significant reduction in alpha-GST after 24 h MP using POLYSOL vs MP using UW-G is demonstrated. Values (N=5) are expressed as mean±SEM.

Figure 6:
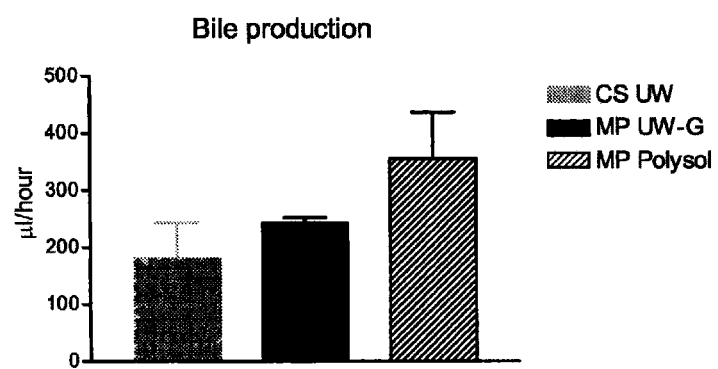

FIG. 6: Bile production during 60 minutes of normothermic reperfusion with KHB. Bile production is increased after MP using POLYSOL when compared to CS in UW and MP using UW-G. Values (N=5) are expressed as mean±SEM.

Figure 7A:
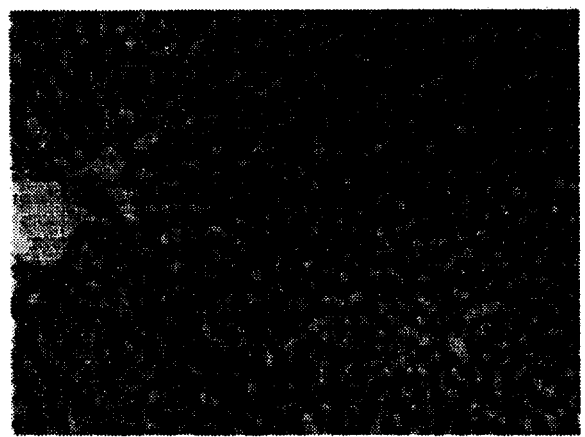

FIG. 7a,b,c: Histopathological appearance of livers following 60 minutes of normothermic reperfusion with KHB: a) After 24 h CS: Widened sinusoids (→), vacuolization in zone 1-3 (O), pycnosis and areas of necrosis; b) After 24 h MP using UW-G: decreased sinusoidal spaces (→), vacuolization in zone 3 (O), no necrosis; c) After 24 h MP using POLYSOL: normal sinusoidal structure and hepatocytes, no vacuolization or necrosis.

Figure 8:
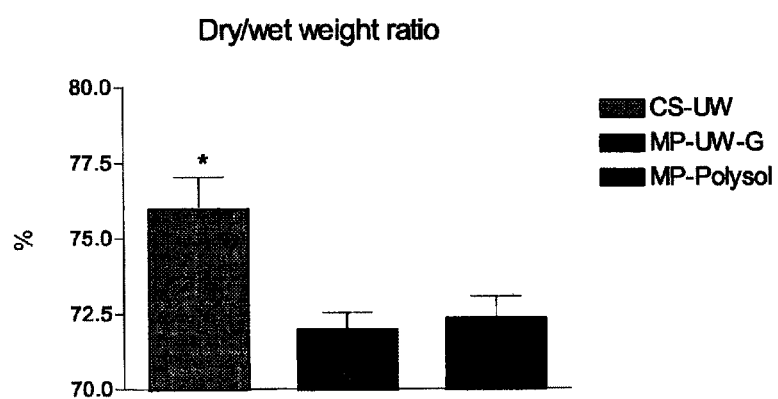

FIG. 8: Dry/wet weight ratio of liver biopsies, after reperfusion (N=5). Dry/wet weight ratio (%) is highest in the CS group as compared to both MP-UW-G and MP-Polysol. Values expressed as mean±SEM.

Figure 9A:
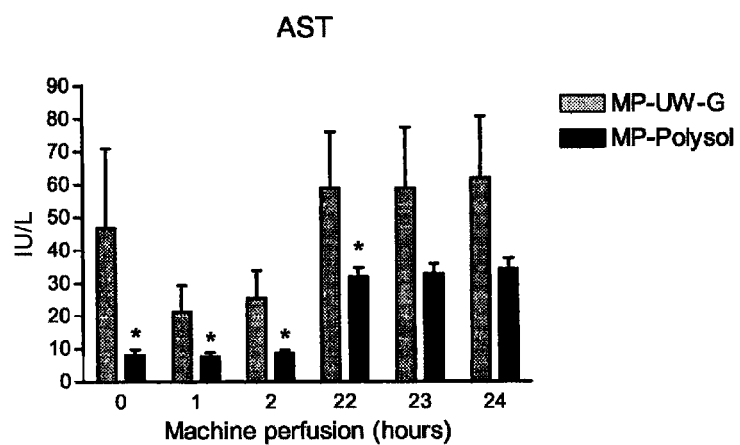
Figure 9B:
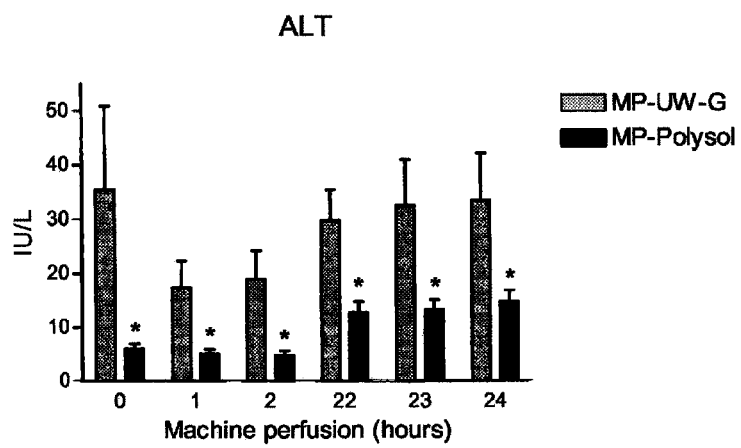

FIG. 9: Release of liver enzymes during 24 hours hypothermic MP of the rat liver. More damage was seen during MP using UW-G as compared to Polysol, regarding both AST and ALT levels.

Figure 10:
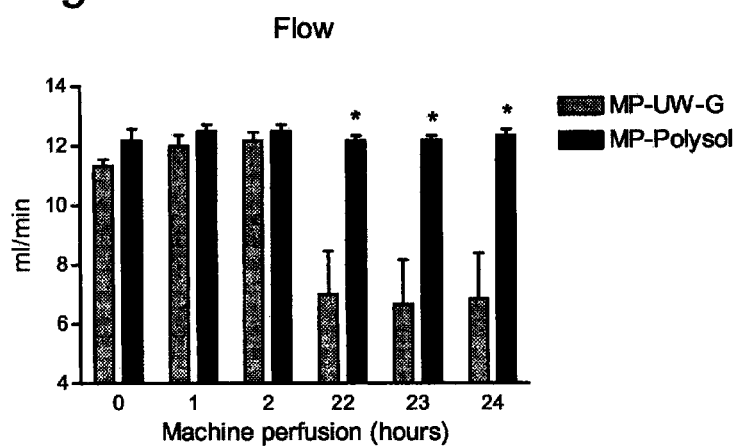

FIG. 10: Perfusate flow during 24 hours hypothermic MP of the rat liver. During the first hours no differences were seen, however, at t=20 hours, livers perfused with UW-G showed significantly lower flow as compared to Polysol.

Figure 11A:
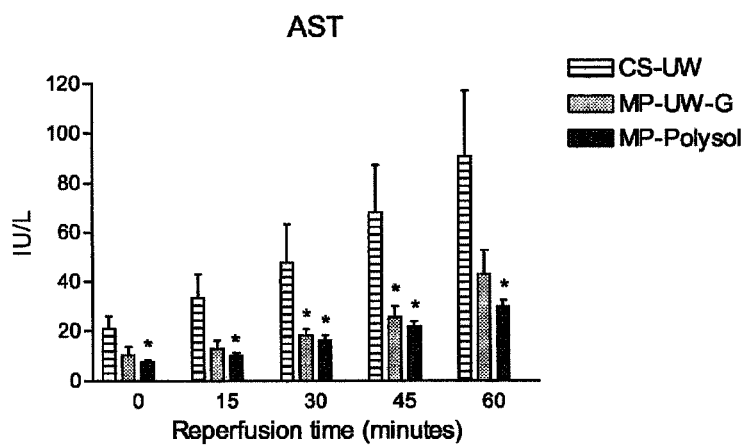
Figure 11B:
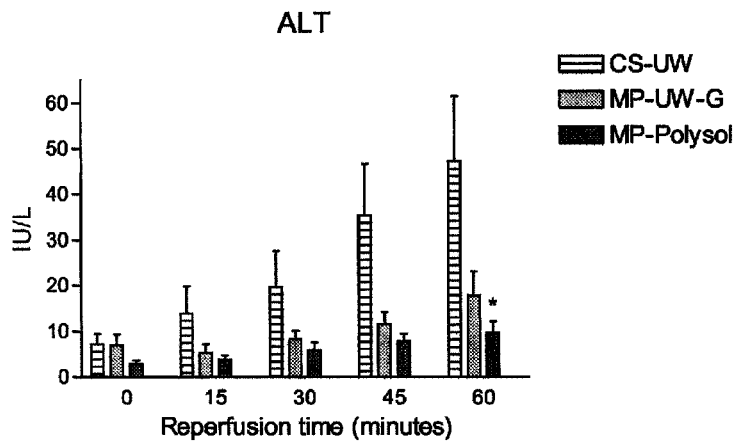

FIG. 11: Release of liver enzymes during 60 minutes normothermic reperfusion of the rat liver, using Krebs-Henseleit buffer. Significantly less release of enzymes was seen in the MP groups. These differences were more obvious when AST was measured as compared to ALT. No significant differences were seen between UW-G and Polysol.

Figure 12:
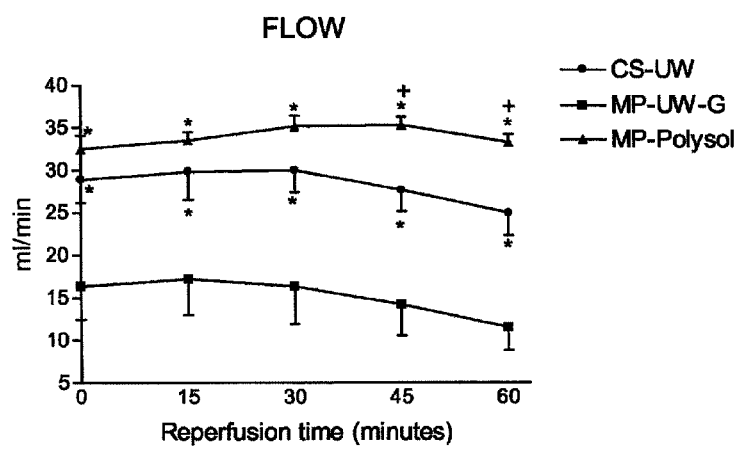

FIG. 12: Perfusate flow during 60 minutes of normothermic reperfusion of the rat liver. The flow was significantly lower in the MP-UW-G group, as compared to both CS-UW and MP-Polysol. Further, perfusate flow in the Polysol group was significantly higher as compared to the CS group, at t=45 and 60 minutes.

Figure 13:
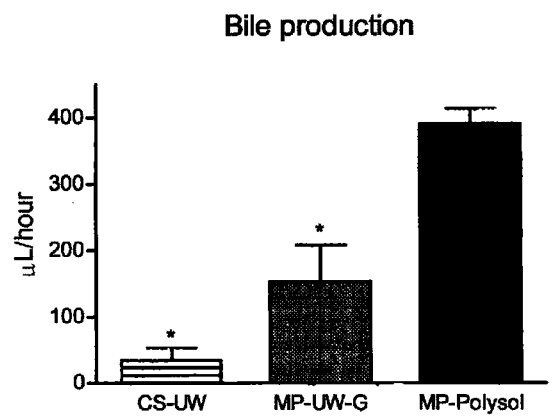

FIG. 13: Bile production during reperfusion. Significantly more bile was produced after MP using Polysol, as compared to both CS and MP-UW-G. Differences between CS and MP-UW-G were not significant.

Figure 14A:
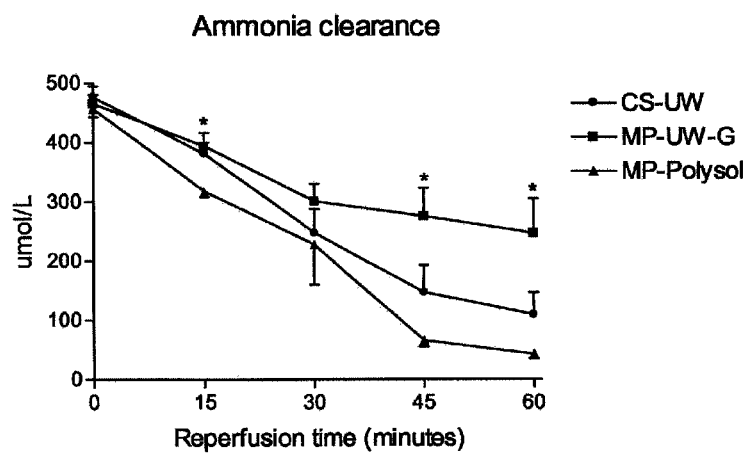
Figure 14B:
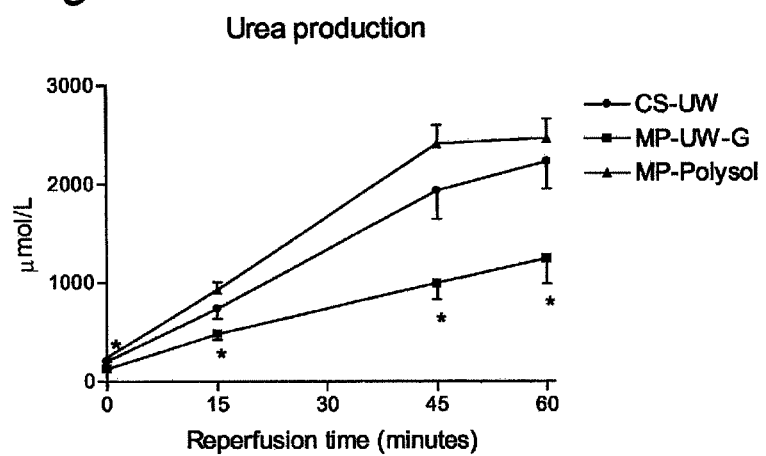

FIG. 14: Ammonia clearance and urea production during reperfusion. Function was measured after challenge of the liver with 5 mM ammonium chloride, added to the perfusate. Ammonia clearance and urea production were significantly lower after MP-UW-G as compared to Polysol.

Figure 15:
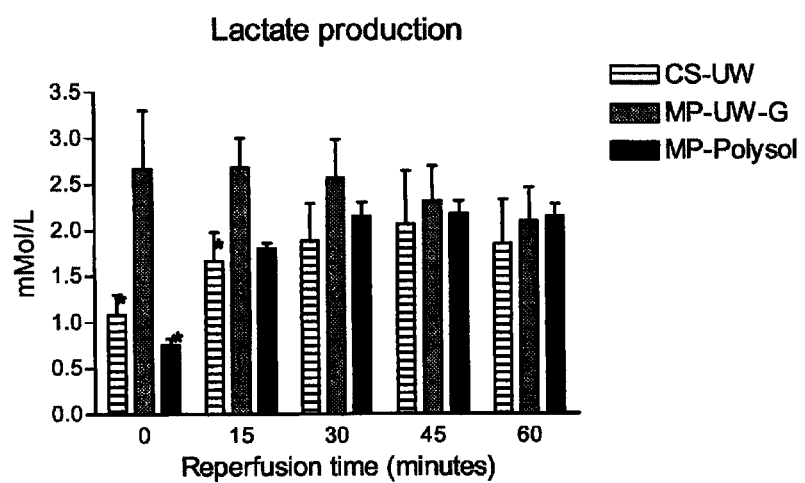

FIG. 15: Lactate production during reperfusion.

Figure 16:
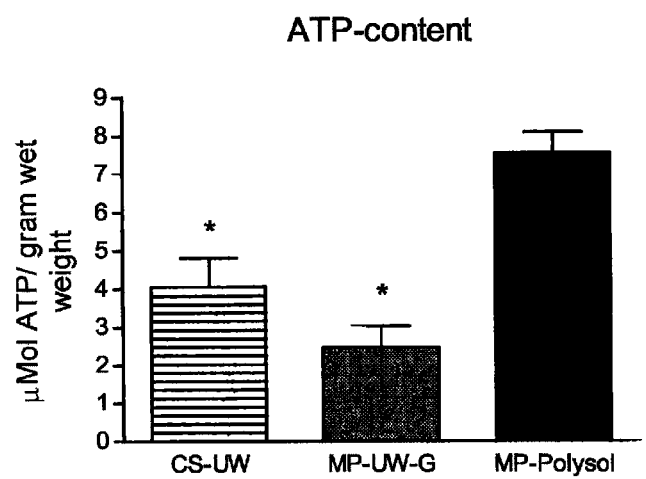

FIG. 16: ATP-content after reperfusion using Krebs-Henseleit buffer. The amount of ATP was highest after MP using Polysol as compared to both CS and MP-UW-G.

Figure 17:
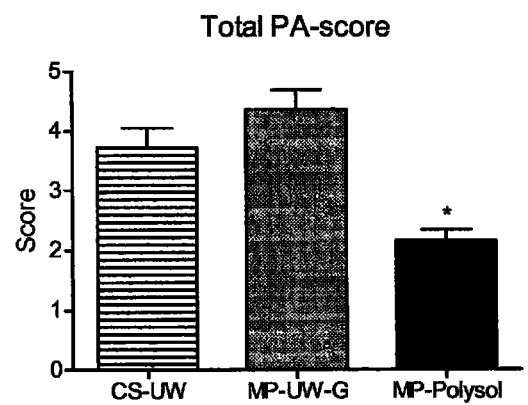

FIG. 17: Histological score of liver biopsies. Semi-quantitative assessment of H&E stained sections resulted in a median score of 2.4±0.3 for liver preserved using Polysol. This was a significantly better score as compared to both CS and MP using UW-G.

Figure 18:
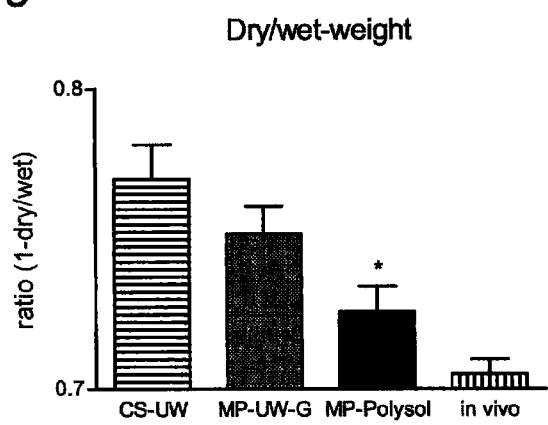

FIG. 18: Dry/wet weight ratios of biopsies taken after reperfusion. Significantly lower dry/wet weight ratios were seen after MP using Polysol, as compared to CS in UW and MP using UW-G.

EXAMPLES

Comparative Example 1

A typical example of a preferred embodiment for an organ preservation and perfusion solution according to the current invention, compared to a widely used tissue culture medium:

| Component | Williams Medium E Liquid mg/L | Polysol 1 Liquid mg/L | Polysol 2 Liquid mg/L |
|---|---|---|---|
| Inorganic Salts | | | |
| $CaCl_2$(anhyd.) | 200.00 | 30.00 | 22.5 |
| $CuSO_4 \cdot 5H_2O$ | 0.00 | x | |
| $Fe(NO_3)_3 \cdot 9H_2O$ | 0.00 | x | |
| KCl | 400.00 | x | |
| $MgSO_4$(anhyd.) | 400.00 | 100.00 | 75.00 |
| $MgSO_4 \cdot 7H_2O$ | 200.00 | 100.00 | 75.00 |
| $MnCl_2 \cdot 4H_2O$ | 0.0001 | 0.0001 | 0.000075 |
| NaCl | 6800.00 | x | 720.00 |
| $NaHCO_3$ | 2200.00 | x | |
| $NaH_2PO_4 \cdot H_2O$ | 140.00 | 1400.00 | |
| $ZnSO_4 \cdot 7H_2O$ | 0.0002 | 0.0006 | |
| KaOH 10N | | | 2.65 ml |
| HCl 1N | | | 2.55 ml |
| Other Components | | | |
| Glucose | 2000.00 | 2000.00 | 1500.00 |
| Glutathione (reduced) | 0.05 | 900.00 | 1500.00 |
| Linoeic Acid Methyl Ester | 0.03 | 0.03 | 0.0225 |
| Phenol Red Na | 10.00 | 10.00 | x |
| Sodium Pyruvate | 25.00 | 25.00 | 18.75 |
| Tween 80 | 1.84 | x | x |

-continued

| Component | Williams Medium E Liquid mg/L | Polysol 1 Liquid mg/L | Polysol 2 Liquid mg/L |
|---|---|---|---|
| Amino Acids | | | |
| L-Alanine | 90.00 | 90.00 | 67.5 |
| L-Arginine | 50.00 | 250.00 | 187.5 |
| L-Asparagine H2O | 20.00 | 120.00 | 90 |
| L-Aspartic Acid | 30.00 | 30.00 | 22.50 |
| L-Cysteine | 40.00 | 40.00 | 30 |
| L-Cystine | 20.00 | 60.00 | 45 |
| L-Glutamic Acid | 50.00 | 50.00 | 37.50 |
| Glycine | 50.00 | 50.00 | 37.50 |
| Histidine | 15.00 | 980.00 | 735.00 |
| L-Isoleucine | 50.00 | 50.00 | 37.50 |
| L-Leucine | 75.00 | 75.00 | 56.25 |
| L-Lysine HCl | 87.50 | 87.50 | 65.625 |
| L-Methionine | 15.00 | 45.00 | 33.75 |
| L-Phenylalanine | 25.00 | 50.00 | 37.50 |
| L-Proline | 30.00 | 90.00 | 67.50 |
| L-Serine | 10.00 | 30.00 | 22.50 |
| L-Threonine | 40.00 | 40.00 | 30.00 |
| L-Thryptophan | 10.00 | 180.00 | 135.00 |
| L-Tyrosine | 35.00 | 35.00 | 26.25 |
| L-Valine | 50.00 | 50.00 | 37.50 |
| Vitamins | | | |
| Ascorbic Acid | 2.00 | 20.00 | 15.00 |
| d-Biotin | 0.50 | 0.50 | 0.375 |
| D-Ca Pantothenate | 1.00 | 1.00 | 0.75 |
| Choline Chloride | 1.50 | 1.50 | 1.125 |
| Ergocalciferol | 0.10 | 0.10 | 0.075 |
| Folic Acid | 1.00 | 1.00 | 0.75 |
| i-Inositol | 2.00 | 12.00 | 9.00 |
| Menadione Na bisulfite | 0.01 | 0.01 | 0.0075 |
| Nicotinamide | 1.00 | 1.00 | 0.75 |
| Pyridoxal HCl | 1.00 | 1.00 | 0.75 |
| DL-Tocopherol phosphate Na | 0.01 | 0.03 | 0.0225 |
| Riboflavin | 0.10 | 1.00 | 0.75 |
| Thiamine HCl | 1.00 | 10.00 | 7.50 |
| Vitamin A Acetate | 0.10 | 0.10 | 0.075 |
| Vitamin B12 | 0.20 | 0.20 | 0.15 |
| Additions | | | |
| $NaSeO_3 \cdot 5H_2O$ | | 0.05 | 0.0375 |
| $MgCl_2 \cdot 6H_2$) | | 731.88 | 548.91 |
| HEPES | | 4766.00 | 4766.00 |
| $KH_2PO_4 \cdot H_2O$ | | 1360.90 | 1020.67 |
| L-Ornithine | | 337.00 | 252.75 |
| Glutamine | | 10 ml/L | 7.5 ml/l |
| Nicotinic Acid | | 0.50 | 0.375 |
| Adenosine | | 1340.00 | 1005 |
| Adenine | | 680.00 | 510.00 |
| Allopurinol | | 163.20 | 122.40 |
| Raffinose | | 1600.00 | 1200.00 |
| Trehalose $\cdot 2H_2O$ | | 2000.00 | 1500.00 |
| D-Gluconic Acid Sodium | | 16358.00 | 12268.50 |
| D-Gluconic Acid Potassium | | 4684.00 | 3513.00 |
| Macrogol PEG 30 | | 25000.00 | 20000.00 |

Na+ content <120 mM
K+ content <25 mM
C− content <50 mM
Osmolarity <340 mosmol
Oncotic pressure 25 mmHg
pH 7.4

Example 2

The aim of this example was to assess machine perfusion (MP) of rat livers using POLYSOL-1, an organ preservation solution according to the current invention and described in example 1, to compare results with machine perfusion using POLYSOL and UW-G, both in relation to the gold standard cold storage (CS) method using UW. To this end, both preservation methods and MP solutions were assessed in the isolated perfused rat liver model (IPRL) from heart beating donors.

Materials and Methods

Animals and Surgery:

Male Wistar rats (Harlan, The Netherlands), weighing 350 g (+/−50 g) were used as liver donors. The animals were housed under standardized conditions with a 12/12 h dark/light circle and ad libitum access to water and a standard pellet chow (Hope Farms, Woerden, The Netherlands), until directly prior to the experiment. All animals were handled in accordance to Dutch regulations and principles of animal care, under approval of the Animal Ethical Committee of the University of Amsterdam.

Rats were anesthetized with $O_2$/air/Isoflurane (1 L/min:1 L/min:3%) and an intraperitoneal injection of 0.1 ml/100 g bodyweight FFM (Hypnorm/Dormicum/aquadest: 1:1:2). During surgery, anesthesia was maintained with inhalation of $O_2$/air/Isoflurane through a mask.

After median laparotomy followed by bilateral subcostal incisions, the liver was mobilized and the bile duct canulated with a 0.9 mm catheter (B-Braun, Melsungen, Germany). Before canulation of the portal vein, the animal was heparinized via the caval vein with 0.1 ml Heparin (5000 IU/ml, Leo Pharma, Malmö, Denmark). The liver was washed out with 50 ml of Ringer Lactate (37° C., 10 cm $H_2O$, Baxter, Utrecht, the Netherlands) via the portal vein canula (0.8 fr, enteral feeding tube, Vygon, Valkenswaard, the Netherlands). During washout the animal was bled via incision of the abdominal caval vein. The suprahepatic caval vein was canulated with a 0.6 fr canula (Vygon), the infrahepatic caval vein ligated and after trimming of surrounding tissue the liver was excised and weighed.

Machine Perfusion System:

A dual machine perfusion system was developed by the Medical Technical Development Department of the Academic Medical Center (AMC, Amsterdam, the Netherlands) enabling both MP and reperfusion (RP) phase in a single set-up (FIG. 1). Prior to connection of the excised liver, the circuit was rinsed with 200 ml of sterile aquadest and subsequently with 50 ml of preservation solution. The pressure controlled perfusion system consists of a reservoir containing 400 ml of sterile MP solution. After connecting the liver to the system, the first 100 ml of perfusion solution was collected. The remaining 250 ml of solution was recirculated by a rollerpump (Ismatec, Glattbrugg, Switzerland). The perfusion solution was oxygenated with carbogen (95% $O_2$/5% $CO_2$, 1 L/min, Hoekloos Medical, The Netherlands) by a glass oxygenator, resulting in a prehepatic oxygen tension of approximately 700 mmHg. Air emboli were removed from the system by a bubble trap, after which the solution was cooled using a heat exchanger (HMT-200, Heto, Breda, the Netherlands). The perfusion solution passed through an in-line flow meter (HT-207, Transonic Systems Inc, Maastricht, the Netherlands), entered the liver through the portal vein canula and runned freely via the suprahepatic caval vein canula into the reservoir.

Reperfusion was performed along the same circuit as described above, with a second reservoir now containing 400 ml of Krebs-Henseleit Buffer (KHB) solution at 37° C. Before re-connecting the liver, the system was rinsed with 200 ml sterile aquadest and 50 ml KHB. After re-connection of the liver, the first 100 ml was drained to prevent it from re-entering the circuit. The remaining 250 ml of perfusate was oxygenated with carbogen. Samples were obtained from the tubing directly pre- or posthepatically. Temperature was recorded by a probe (Laméris, The Netherlands) placed under the liver. After each procedure, the circuit was rinsed and steam-sterilized (134° C. for 16 minutes).

Experimental Groups and Preservation Conditions:

This study comprised of 3 experimental groups: 1) CS-UW (N=5); 2) MP-UW-G (N=5) and 3) MP-POLYSOL (N=5). The isolated livers were preserved by either CS or MP for 24 hours and thereafter reperfused.

After wash-out with RL (4° C.), the liver was flushed in situ with the preservation solution. CS livers were flushed with 50 ml UW (4° C.), placed in a sterile cup containing 100 ml of UW and stored on melting ice in a cold chamber (4° C.) for 24 hours. MP livers were connected to the perfusion system via the portal vein directly after wash-out and harvesting, flushed with 100 ml of either UW-G or POLYSOL and continuously perfused with this solution at 4° C. for 24 hours. After the preservation period, all livers were reperfused for 60 minutes at 37° C. with oxygenated KHB.

Preservation Solutions:

For cold storage, the University of Wisconsin preservation solution (Viaspan, Bristol Myers Squibb) was used. The UW-G solution for MP was prepared according to Belzer's prescription (pH 7.4, 330 mosmol/kg) (Pienaar B H et al., Transplantation 1990:49: 258-260). The MP preservation solution POLYSOL (pH 7.4, 330 mosmol/kg) was developed at the Surgical Laboratory of the AMC. For reperfusion, Krebs-Henseleit Buffer (KHB), without bovine serum albumin (pH 7.4, 320 mosmol/kg) was used.

UW-G, POLYSOL and KHB were all prepared in our laboratory using analytical reagent grade (or better) chemicals from Sigma-Aldrich (Zwijndrecht, The Netherlands), Merck (Haarlem, The Netherlands), Cambrex (Verviers, Belgium), Centrafarm (Etten-Leur, The Netherlands) and Novo Nordisk (Alphen aan den Rijn, The Netherlands). The Hydroxyethylstarch (HES) was obtained from Fresenius (Taunusstein, Germany). Prior to use, the solutions were sterilized by filtration through a 0.45 µm ampul filter (DowCorning, Allesley, United Kingdom) and a 0.22 µm filter (Millipack 60, Millipore, Amsterdam, the Netherlands).

Assessment of Hepatocellular Damage and Liver Function:

Samples for hepatocellular damage assessment were taken every 10 minutes during 60 minutes of RP.

Liver damage was assessed by direct analysis of aspartate aminotransferase (AST), alanine aminotransferase (ALT) and lactate dehydrogenase (LDH) in posthepatic perfusate samples (Laboratory of Clinical Chemistry, AMC, the Netherlands). Alpha-GST (alpha-glutathione-S-transferase) levels were determined using a rat alpha-GST ELISA kit (Biotrin, Dublin, Ireland).

Liver function was assessed by monitoring bile production during 60 minutes of RP. Furthermore, lactate production (Laboratory of Clinical Chemistry, AMC, the Netherlands) indicating anaerobic glycolysis and perfusate pH (ABL, Radiometer, Zoetermeer, The Netherlands) were measured during reperfusion.

Histology and Dry/Wet Weight Ratio:

At the end of the RP phase biopsies were taken from the caudate and right lateral lobes. Biopsies were stored in formaldehyde (10%) and embedded in paraffin.

Paraffin sections (4 µm) were stained with hematoxylin and eosin (H&E) and evaluated with light microscopy. A 9-point scale was used for morphological classification of hepatic injury graded on a scale of 1 (excellent) to 9 (poor) (Martin H, et al., Cryobiology 2000:41: 135-144, and Tojimbara T et al., Liver Transpl Surg 1997:3: 39-45.) 1. normal rectangular structure, 2. rounded hepatocytes with an increase of sinusoidal spaces, 3. vacuolization in zone 3, 4. vacuolization in zone 2, 5. vacuolization in zone 1, 6. vacuolization and nuclear pycnosis in zone 3, 7. vacuolization and nuclear pycnosis in zone 2, 8. vacuolization and nuclear pycnosis in zone 1 and 9. necrosis.

For dry/wet weight ratio's liver biopsies were weighted immediately after reperfusion and were thereafter stored in a 60° C. stove. Biopsies were weighed again every 7 days, until reduction of liver weight had stopped. To demonstrate the amount of liver edema, the following calculation was used: 1−(dry weight/wet weight)×100%.

Statistical Analysis:

The Kruskall-Wallis test was used for overall comparison of the three groups. If significant differences were shown, differences between individual groups were evaluated by the non-parametric Mann Whitney test. Results in text and graphs are shown as mean±SEM. Statistical significance was defined as $p<0.05$.

Results

Perfusion Parameters:

Liver weights did not differ significantly between experimental groups (16.53±0.53 gram). During both hypothermic MP and normothermic RP the perfusion pressure was constantly kept at 20 cm $H_2O$ (gravity controlled). The perfusion flow during hypothermic MP reached 1 ml/min/gram liver maximally. During normothermic RP a maximum flow of 4 ml/min/gram liver was recorded. Oxygenation during hypothermic MP resulted in a perfusate $pO_2$ of approximately 700 mmHg and during normothermic RP, due to the higher temperature, in a $pO_2$ of approximately 500 mmHg. The temperature recorded during normothermic RP was 37.13±0.41° C.

Hepatocellular Damage:

ALT release after 24 hours cold ischemic time was significantly higher after CS with UW as compared to MP using UW-G at t=0' (4.6±5.37 vs 0.4±0.55) and t=10' (5.4±3.85 vs 1.4±0.55 U/L) (FIG. 2). However, when CS-UW is compared to MP-POLYSOL, ALT levels are significantly lower after MP-POLYSOL, at all time points except t=0' and t=50'. LDH levels appear higher after 24 hours CS-UW, without reaching significancy. LDH is significantly higher after CS-UW at t=10' (FIG. 3) as compared to MP using either UW-G or POLYSOL. Perfusate flow, pH and lactate production were not significantly different (data not shown).

When comparing the two MP solutions, less damage after 24 hours of MP-POLYSOL was seen, as shown by the lower AST levels (FIG. 4). Although there was a trend in favour of Polysol at all time points, there were no significant differences in ALT, LDH, flow, pH and lactate.

Release of α-GST (FIG. 5) at t=40 was lower after MP-POLYSOL as compared to CS-UW (125.5±10.51 vs 46.35±9.11, respectively, p<0.02) and to MP-UW-G (101.6±11.99 vs 46.35±9.11, respectively, p<0.02).

Hepatocellular Function:

Bile production was higher after MP-POLYSOL than after MP-UW-G or CS-UW (355±82.31 versus 256±26.19 versus 180±61.89 µl, respectively). However, this did not reach significancy (FIG. 6).

Figure 7B:
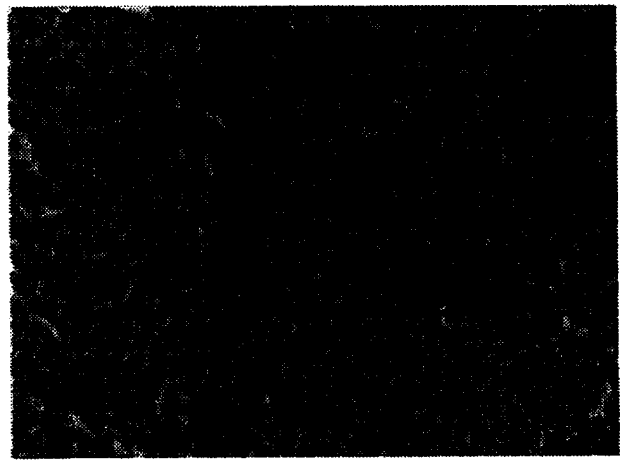
Figure 7C:
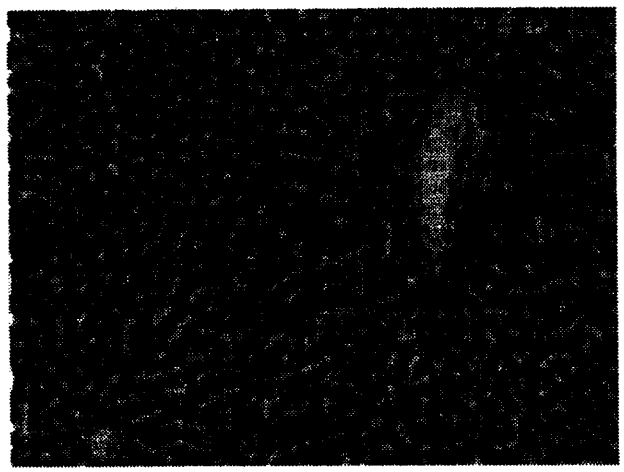

Histology:

After histopathological scoring of the liver sections, a better median score was assigned to the MP groups using UW-G and POLYSOL (2.0±0.55 and 1.6±0.40 points respectively) as compared to the CS-UW livers (4.5±0.87 points) (p=0.06 for UW-G and p=0.03 for POLYSOL). There were no significant differences between the MP groups (FIG. 7).

The dry/wet weight ratio of liver sections was highest in the MP groups, accounting for the lowest percentage of edema (FIG. 8). Percentages were 76±1.0 versus 72±0.5 versus 72±0.7 respectively.

Conclusions

For clinical MP of the kidney, the modified University of Wisconsin solution (UW-Gluconate) is normally used. This solution has been further modified for application of MP in the liver, by substituting mannitol with raffinose. The resulting solution has been extensively used in experimental liver preservation (Kim J S et al., Transplant Proc 1997:29: 3452-3454, Pienaar B H et al., Transplantation 1990:49: 258-260, Southard J H et al., Transplant Proc 2000:32: 27-28.) (1-3) but is not commercially available. The new preservation solution for MP of liver and kidney according to the current invention, POLYSOL, containing the nutrients which are according to the inventors necessary to support the suppressed metabolism at 4° C., was examined. Although our ultimate goal is the preservation of organs of marginal and non heart-beating donors, which is addressed in example 3, we first sought to test POLYSOL in a well established heart-beating-donor model, in order to obtain base-line values.

In this example we have shown the benefits of MP over CS, in a heart-beating-donor rat liver model. Hepatocellular damage was significantly lower in the MP preserved livers. This can be explained by the continuous oxygenation of the perfusion system and the continuous supply of nutrients during MP, Furthermore, liver function as expressed by bile production is improved after 24 hour MP.

MP using POLYSOL resulted in lower hepatocellular damage values and improved post preservation function, in terms of bile production. We have enhanced the buffering capacity of the solutions according to the invention, optimized oxygen-free radical scavenger contest and added specific nutrients for amino acid, energy and fat metabolism. Furthermore, the solution is prepared with pH 7.4, but after connection to the oxygenated liver the pH decreases to pH 7.2.

In conclusion, preservation of the heart-beating donor rat liver by machine perfusion results in a better quality liver preservation as compared to cold storage. Machine perfusion using a new, enriched preservation solution according to the invention, POLYSOL-1, results in better quality liver preservation when compared to UW-G. In this example Polysol-1 was used, as defined in example 1. Polysol refers to polysol-1.

Example 3

The aim of this example is to compare preservation of the non-heart-beating donor (NHBD) rat liver with CS using UW, MP using UW-G and MP using Polysol-1.

The historical preservation method of choice for the optimal donor liver is cold storage. Recent studies have however shown that preservation by continuous hypothermic machine perfusion (MP) results in less liver damage and better liver function after 24 hours preservation (Kim J S et al., Transplant Proc 1997; 29(8):3452-3454, Southard J H et al, Transplant Proc 2000; 32(1):27-28, Xu H. et al., Transplantation 2004; 77(11):1676-1682.) (4-6) The advantages of MP can be found in the supply of nutrients and oxygen to the donor organ, the possibility of viability assessment during preservation and before implantation. Another advantage can be found in the possible resuscitation of NHBD organs. These ischemically damaged organs are difficult to preserve by CS, resulting in liver damage and decreased liver function after preservation. The preservation solution used for machine perfusion of the liver, in experimental settings is the modified University of Wisconsin solution, UW-gluconate (UW-G). (Marsh D C, et al., Cryobiology 1989; 26(6):524-534, Pienaar B H, et al., Transplantation 1990; 49(2):258-260.) This solution contains the colloid hydroxyethylstarch, which causes microcirculatory disturbances, is hard to obtain and expensive. UW-G does not provide the liver with sufficient amounts of nutrients, to support the decreased metabolism at low temperatures, for instance at 4° C. We have therefore developed a new preservation solution according to this invention for MP of liver and kidney, based on the colloid polyethyleneglycol, containing a tissue culture medium with necessary nutrients for the liver in sufficient quantities to be taken up at low temperatures, with enhanced buffering capacity and enhanced anti-oxidant compounds to prevent reperfusion injury and to minimize the effects of ischemia, hypoxia, acidification and nutrient depletion sustained by organs obtained from non heart-beating donors.

TABLE 1

The most important components of UW, UW-G and Polysol

| | Components: | | |
|---|---|---|---|
| | UW | UW-G | Polysol |
| Colloid | HES (5%) | HES (5%) | PEG (1%) |
| Na/K ratio | 30/120 mM | 125/25 mM | 120/20 mM |
| Buffer | $KH_2PO_4$ | HEPES | HEPES |
| | | $KH_2PO_4$ | $KH_2PO_4$ |
| | | | Histidine |
| Antioxidants | Allopurinol | Allopurinol | Glutathion |
| | Glutathion | Glutathion | Alpha-tocopherol |
| | | | Ascorbic acid |
| Energy substrates | | Glucose | Glucose |
| Impermeants | Lactobionate | Na-Gluconate | Na-Gluconate |
| | | K-Gluconate | K-Gluconate |
| | | Mg-Gluconate | |
| | Raffinose | Raffinose | Raffinose |
| | | | Trehalose |
| Amino acids | — | — | Various |
| Vitamines | — | — | Various |
| pH-indicator | — | — | Phenol-red |

Materials and Methods

Animals:

Male Wistar rats (Harlan, The Netherlands), weighing 275 g (+/−25 g) were used as liver donors. The animals were housed under standardized conditions with a 12/12 h dark/light circle and free access to water and a standard pellet diet (Hope Farms, Woerden). All animals were handled in accordance to Dutch legislations and principles of animal care. The Animal Ethical Committee of the University of Amsterdam approved for this animal study.

Experimental Groups and Preservation Conditions:

24 Hour liver preservation of the NHBD liver was performed by either CS using UW (n=6), MP using UW-G (n=6) or MP using Polysol (n=6). After the in vivo washout with Ringer Lactate at 37° C. the liver was flushed with the hypothermic preservation solution (4° C.): the liver was flushed with 50 ml of either UW, UW-G or Polysol. For CS the liver was placed floating in a plastic sterile cup, containing 100 ml of hypothermic UW, placed on melting ice in a cold chamber at 4° C. For MP the liver was connected to a recirculating standardized perfusion set-up, containing 250 ml of preservation solution, which was circulated from a reservoir by a roller pump, oxygenated with carbogen (95% $O_2$/5% $CO_2$) and cooled by a heat exchanger to an inflow temperature of 4 degrees. Outflow of the perfusate was collected via the caval vein and re-entered the reservoir. Both during MP as well as during reperfusion (RP) samples were taken for the assessment of liver damage and function.

Preservation Solutions:
As in example 2.
Surgical Procedure:
As in example 2.
Machine Perfusion System:
As in example 2.
Sample Preparation:

Perfusate samples for hepatocellular injury and function assessment were taken during MP and RP. During MP the samples were taken hourly at t=0, 1, 2, 22, 23, 24 hours. In the RP phase the samples were taken with 15 minute intervals during 60 minutes. At the end of the reperfusion phase liver samples for ATP-assessment were taken from the accessory liver lobe using a freeze clamp for immediate freezing. Liver samples were further obtained from the caudate and right liver lobes and were processed in formalin (10% in PBS). Liver samples for transmission electron microscopy were obtained from the median lobe and stored in Mac Dowall solution. Finally liver samples were taken from the left lobe for dry/wet weight analysis.

Liver Damage and Liver Function Studies:
As in example 2.

Damage: Liver damage was assessed by spectrophotometric analysis of aspartate aminotransferase (AST) and alanine aminotransferase (ALT). Perfusate flow was measured during MP and RP in order to describe vascular integrity.

Function: liver function was assessed (during the RP phase) by measuring bile production, oxygen consumption, ammonia clearance, urea production and ATP-restoration.

Oxygen consumption was determined by the difference in oxygen tension in pre- and posthepatic bloodgas samples (ABL, Radiometer, Zoetermeer, The Netherlands). For bile production bile was collected via the bile duct canula during every 15 minutes. To measure ammonia clearance and urea production the liver was challenged with 5 mM ammonium chloride (Sigma-Aldrich, Zwijndrecht, The Netherlands). Samples were taken at t=-5, 0, 15, 30, 45 and 60 minutes of RP. To analyse ammonia clearance the samples were processed on ice after dilution (10×) with phosphate buffered saline and acidification with 0.275% HCl. A microdiffusion method using broomcresolgreen as indicator was used. Urea production was analysed with a colorimetric method, based on the reaction between diacetylmonoxime and certain nitrogenous compounds (such as urea, methylurea, citruline) (Sigma-Aldrich). ATP-values were measured in freeze clamped biopsies, which were pulvered under liquid nitrogen, diluted in perchloric acid (14%) and thereafter analysed after addition of Hexokinase and G6PD.

Histology:
As in example 2, except:

Liver biopsies (1 mm) for Transmission Electron Microscopy (TEM) were obtained from the left lateral lobe. For ultrastructural investigation biopsies were fixed in McDowells fixative for at least 48 hours. Thereafter they were rinsed in phosphate buffer (0.1 M, pH 7.4) postfixed in 1% $OsO_4$, rinsed in water and dehydrated in graded ethanols and propylene oxide. Finally the specimen were embedded in epon. Ultrathin sections (80 mm) were cut with a Reichert Ultracut E and contrasted with uranyl acetate and lead citrate. Sections were studied with a Philips EM420 operated at 100 kV; images were acquired with a SIS Megaview II camera.

Statistical Analysis:

All groups were compared using the Kruskall-Wallis test. In case of significant outcome, differences between individual groups were evaluated by the non-parametric Mann Whitney-U test. For the ammonia clearance rate an analysis for repeated measurements was used, with a post-hoc test according to Bonferroni. Results in text and graphs are shown as mean±SEM. Statistical significance was defined as $p<0.05$.

Results

No differences in rat weight and liver weight were seen within experimental groups. Reperfusion temperatures did not differ between groups.

Hepatocellular Damage (MP):

During MP the release of AST was significantly higher using UW-G, as compared to Polysol, at t=0, 1, 2 and 22 hours. ALT release was significantly higher using UW-G as compared to Polysol at all time points (FIG. 1a,b).

Perfusate flow during MP decreased in the MP-UW-G group, resulting in a lower flow at t=22, 23 and 24 hours as compared to MP-Polysol (p=0.01) (FIG. 2).

Hepatocellular Damage (RP):

AST release (FIG. 3a) was lower after MP-UW-G as compared to CS, on t=30 and t=45 (p<0.05). Using Polysol this release was lower at all time points (p<0.005). ALT release showed the same trend (FIG. 3b), but significancy was only reached at t=60 for MP-Polysol as compared to CS (24.67±7.30 vs. 6.00±1.26 IU/L, p=0.05).

Perfusate flow during RP was significantly better with MP-Polysol as compared to CS on t=45 and 60 and to MP-UW-G at all time points (FIG. 4). Also perfusate flow was better in the CS group as compared to MP-UW-G at all time points (p<0.05).

Hepatocellular Function (RP):

Bile production was highest after MP using Polysol as compared to CS with UW and MP using UW-G (390±23 vs. 34±19 vs. 153±55 µl/hour respectively, p<0.01). No significant difference was seen between CS-UW and MP-UW-G (FIG. 5).

The most ammonia clearance occurred after MP using Polysol, which was significantly better then using UW-G at t=15, 45 and 60 and then CS at t=15. Urea production was significantly higher in the Polysol groups as compared to UW-G at all time points. There were no differences between Polysol and CS, however, more urea produced in the CS group as compared to UW-G at t=45 (FIG. 6a,b).

Lactate production was higher after MP using UW-G at t=0 and 15, compared to both CS and MP using Polysol. No differences were seen at later time points (FIG. 7). Oxygen consumption was equal for all groups during the reperfusion phase (data not shown).

ATP-Measurements:

ATP-content at the end of the reperfusion phase was significantly higher after MP using Polysol, as compared to both CS in UW and MP using UW-G (7.53±0.55 versus 4.05±0.75 versus 2.46±0.57 µMol/gram wet weight, respectively) (FIG. 8).

Histology:

Semi-quantitative assessment of H&E stained sections as shown in FIG. 9 resulted in a median score of 2.4±0.3 for liver preserved using Polysol. This was a significantly better score as compared to both CS and MP using UW-G (3.9±0.24 and 4.3±0.48 respectively).

Dry/Wet Weight Ratio:

Biopsies taken after reperfusion showed significantly lower dry/wet weight ratios after preservation by MP using Polysol, as compared to CS in UW and MP using UW-G (73±0.01 versus 77±0.01 versus 75±0.01%, respectively) (FIG. 10).

Conclusions

In this example three preservation methods for the NHBD rat liver were compared, the state of the art gold standard CS using UW, MP using UW-G and MP using the newly developed MP preservation solution according to the current invention; Polysol-1. Both regarding liver damage and liver function, the results were significantly better after 24 hours MP using Polysol-1, as compared to CS and MP using UW-G. Concluding, the 24 hour machine perfusion preservation of the NHBD liver using the newly developed preservation solution Polysol-1 according to the current invention results in less liver damage and better liver function as compared to cold storage in UW and machine perfusion using UW-G. In this example, polysol-1 formulation as defined in example 1 was used, and polysol refers to polysol-1.

Example 4

The aim of this study was to assess the feasibility of Polysol in a pig liver preservation model. To this end, MP using Polysol was compared with CS using Celsior. For this and subsequent examples 5 and 6, the polysol-2 formulation was used, as defined in example 1.
Materials and Methods
Animals and Anaesthesia:
Female Landrace pigs weighing 35-45 kg, were used as liver donors. The animals were allowed to acclimatize to the laboratory environment for 7 days, under standardized conditions, with standard laboratory food and water at libitum. Before use in experiments, pigs were fasted overnight, with free access to water. All animals were handled in accordance to Dutch regulations and principles of animal care. Approval for this study was obtained from the Animal Ethical Committee of the University of Amsterdam.

After premedication with ketamine (10 mg/kg), dormicum (1 mg/kg) and atropine (0.1 mg/kg), anaesthesia was induced by inhalation of $O_2/N_2O$ and isoflurane (1-3%). Endotracheal intubation was performed for controlled mechanical ventilation. Anaesthesia was maintained by administration of sufentanil citrate (20 mg/L) and ketamine (20 g/L). For venous access, the ear vene was cannulated. Arterial blood pressure was monitored via the subclavian artery and controlled by fluid infusion.

Operation:
After midline laparotomy and cannulation of the common bile duct (0.8 Fr, enteral feeding tube, Vygon, Valkenswaard, The Netherlands), vascular isolation of the liver was performed. The infrahepatic and suprahepatic parts of the caval vein were dissected for 3-5 cm, the portal vein was dissected distally to the upper pancreatic border and the hepatic artery was dissected downwards to the branching point of the splenic artery from the celiac axis. After heparinization of the pig with 250 IU/kg heparin (5000 IU/ml, Leo Pharma, Malmö, Denmark), the portal vein was cannulated with a silicone tube. The liver was then flushed in vivo with 5 L of ice-cold Ringer Lactate (Lactate 29 mmol/L, $Na^+$ 131 mmol/L, $K^+$ 5.4 mmol/L, $Ca^{++}$ 1.8 mmol/L, $Cl^-$ 111 mmol/L, Baxter, Utrecht, The Netherlands), which was pumped through the liver by a roller pump (Gambro Instruments AB, Lund, Sweden) at a flow of 100-200 ml/min. During this wash-out, the liver was excised and placed in an organ chamber. Subsequently, the liver was either flushed with 1 L of ice-cold Celsior for CS or Polysol for MP, followed by 24 h hypothermic preservation by the respective method.

Solutions (Addendum 1):
The CS preservation solution Celsior (pH 7.3, 320 mOsm/kg) was obtained from Imtix Sangstat (Lyon, France). Our MP preservation solution Polysol was developed at the Surgical Laboratory of the Academic Medical Center (Amsterdam, The Netherlands) (pH 7.4, 312 mOsmol/kg). Polysol was produced by Cambrex (Venviers, Belgium). Krebs-Henseleit buffer (KHB) was prepared in our laboratory using analytical reagent grade chemicals from Sigma-Aldrich (Zwijndrecht, The Netherlands) and Merck (Haarlem, The Netherlands). KHB was sterilized through a 0.22 µm filter (Millipack 60, Millipore, Amsterdam, The Netherlands).

Cold Storage and Hypothermic Machine Perfusion Set-Up:
After wash-out, livers in the CS group (n=5) were placed in a sterile chamber filled with 1 L of ice-cold Celsior, and were stored at 4° C. For MP using Polysol (n=5) livers were placed at 4° C. in an organ chamber which also served as a reservoir, with connections for the perfusate to the portal vein. Polysol was recirculated by a roller pump (200 ml/min, Gambro Instruments AB, Lund, Sweden) and oxygenated by a capillary oxygenator (1 L/min, 100% medical oxygen, Hoekloos Medical, Amsterdam, The Netherlands) to an oxygen tension of 800-1000 mmHg. Polysol entered the liver after passing through a flow sensor (HT-207, Transonic Systems Inc, Maastricht, The Netherlands) and an intraluminal pressure sensor (Baxter, Utrecht, The Netherlands) Perfusate drained freely from the caval vein into the reservoir. A temperature probe (Laméris, Nieuwegein, The Netherlands) was placed in the liver hilum. Perfusate samples were obtained prehepatically.

Normothermic Pig Liver Reperfusion Set Up:
Normothermic reperfusion using oxygenated KHB was performed after 24 h preservation and 30 min rewarming.
The reperfusion was performed in the same set up as MP (see above), but the system was now heated to 39° C. by a heat exchanger (HMT-200, Heto, Breda, The Netherlands). The reservoir was filled with normothermic KHB and the perfusate was oxygenated with carbogen (1 L/min, 95/5% $O_2/CO_2$, Hoekloos Medical, Amsterdam, The Netherland) using a Medos Hilite 800 oxygenator (Stolberg, Germany). The reperfusion flow was set at approximately 500 ml/min.

Analytical Studies:
Hepatocellular Damage:
Levels of aspartate aminotransferase (AST), alanine aminotransferase (ALT) and lactate dehydrogenase (LDH) were determined spectophotometrically in prehepatic perfusate samples with 15 min intervals (7). Intravascular resistance (R) was calculated from the perfusate flow (F, in ml/min) and the intraluminal pressure (P in mmHg) (R=P/F). The intravascular resistance is a parameter for sinusoidal endothelial cell damage and vascular integrity.

Liver Function:
Bile production was measured by collection of bile during reperfusion, in 15 min periods. Ammonia clearance and urea production were measured after challenge of the liver with a single dose of 5 mM ammonium chloride (Sigma-Aldrich, Zwijndrecht, The Netherlands) at the beginning of reperfusion. Samples were taken at t=0, 15, 30, 45 and 60 min of reperfusion. For analysis of ammonia clearance the samples were processed on ice after dilution (10×) with phosphate-buffered saline and acidification with HCl (final concentration: 0.45% m/v). An enzymatic method based on the reaction between ammonia, ketoglutarate and NADPH, catalyzed by glutamate dehydrogenase, was used (8). Urea production was analysed with a colorimetric method, based on its reaction with diacetylmonoxime (Sigma-Aldrich) (9). Lactate production was measured spectofotometrically in perfusate samples. Perfusate pH was measured using a Radiometer blood gas meter (Zoetermeer, The Netherlands).

Statistical Analysis:
Experimental groups were compared by a non-parametric Mann Whitney-U test, using GraphPad Prism, version 4 for Windows (GraphPad Software, San Diego, Calif., USA). For ammonia clearance and urea production rates an analysis for repeated measurements was used, with a post-hoc test according to Bonferroni. Results in text and graphs are shown as mean±SEM, Statistical significance was defined as p<0.05.

Results:

General:

Weight of pigs did not differ between the CS and MP groups (41±3 versus 37±1 kg, respectively). Liver weights after wash-out were 1100±65 and 950±38 g, for CS and MP groups, respectively. Mean reperfusion temperature was similar in both groups (37.3±0.2 and 37.8±0.1° C., respectively).

Liver Damage:

AST levels were significantly higher after CS using Celsior, as compared to MP using Polysol (FIG. 1A). Similar results were obtained for ALT (FIG. 1B). For LDH release, a trend in favor of Polysol was seen, these results, however, were not significant (FIG. 1C).

Intravacular Resistance (FIG. 2):

At t=0 min of reperfusion, intravascular resistance was significantly lower after 24 h MP using Polysol as compared to CS using Celsior. When overall resistance during reperfusion was compared between these groups, resistance was also significantly lower in the CS group (0.13±0.01 and 0.16±0.01 mmHg/ml/min, respectively).

Liver Function:

No bile was produced in both experimental groups. However, all ammonia was cleared during 60 min of reperfusion, with conversion into urea (FIG. 3). No differences between experimental groups were seen. At the end of reperfusion high levels of lactate were seen in both groups, without any difference between CS and MP (8.6±2.3 versus 9.5±1.1 mmol/L). A resultant decreased pH was seen in both groups (6.9±0.1 versus 6.8±0.1).

In conclusion: Pig liver preservation by the newly developed machine perfusion preservation solution Polysol, resulted in equal to better preservation quality as compared to cold storage using Celsior. Polysol appears feasible as a machine perfusion preservation solution for the pig liver.

Example 5

The indications for liver transplantation have expanded during the past years without a concomitant increase in donor organ availability, resulting in growing waiting lists for liver transplantation. While awaiting a donor liver, 14% of patients succumb (10). To reduce the waiting lists several options have been explored, including living donor liver transplantation, split liver transplantation, change of the political system of organ donation and the use of marginal donor livers (11-14). The latter category consists of elderly donors, donors with liver fibrosis or steatosis, or non-heart-beating donors (NHBD) (15-17). In the NHBD, circulatory arrest has occurred before organ procurement.

The current preservation method of choice for the optimal, heart-beating donor liver is cold storage (CS). Recent studies, however, have shown that preservation by continuous hypothermic machine perfusion (MP) results in less liver damage and better liver function after 24 h of preservation (18-20). The advantages of MP have been attributed to the continuous supply of nutrients and oxygen to the donor organ, resulting in resuscitation of NHBD organs. A further advantage is the possibility of viability assessment during preservation. CS is less effective for the preservation of ischemically damaged NHBD organs, since liver damage is enhanced and liver function is decreased during the period of cold ischemia. The preservation solution mainly used for machine perfusion of the liver, in both clinical and experimental settings, is the modified University of Wisconsin solution, i.e. UW-gluconate (UW-G) (21,22). This solution contains the colloid hydroxyethylstarch (HES), which is known to cause microcirculatory disturbances (23), is difficult to obtain and is expensive. UW-G does not provide the liver with specific nutrients to support the metabolic activity of the liver at 4° C., even though metabolism is greatly decreased at this temperature (24). To overcome these shortcomings we have developed a new preservation solution for MP of liver and kidney: it contains, in addition to the colloid polyethyleneglycol, nutrients such as glucose and amino acids which are required for the liver (Addendum 1). In previous studies we have reported a higher quality liver preservation using Polysol over UW-G in a heart-beating donor model (25). In a rat liver model, MP using Polysol resulted in less liver damage and better liver function after 24 h of hypothermic continuous MP.

The aim of this study was to compare preservation of the NHBD rat liver by CS using UW with MP using either UW-G or Polysol.

Materials and Methods

Animals

Male Wistar rats (Harlan, Horst, The Netherlands), weighing 275 g (+/−25 g) were used as liver donors. The animals were housed under standardized conditions with a 12/12 h dark/light cycle and free access to water and a standard pellet diet (Hope Farms, Woerden), until the beginning of the experiment. All animals were handled in accordance to Dutch legislations and principles of animal care. The Animal Ethical Committee of the University of Amsterdam approved this animal study.

Experimental Groups and Preservation Conditions 24 h liver preservation of the NHBD liver was performed by either CS using UW (n=6), MP using UW-G (n=6) or MP using Polysol (n=6).

After in situ wash-out with 50 ml Ringer Lactate (Lactate 29 mmol/L, Na 131 mmol/L, K 5.4 mmol/L, Ca 1.8 mmol/L, Cl 111 mmol/L, Baxter, Utrecht, The Netherlands) at 37° C., the liver was flushed with one of the hypothermic preservation solutions (4° C.), with either 50 ml UW, UW-G Or Polysol at a pressure of 15 mmHg. For CS the liver was immersed in a plastic sterile cup containing 100 ml of UW, placed on melting ice in a cold chamber at 4° C. For MP the liver was connected to a recirculating standardized perfusion set-up, containing 250 ml of preservation solution. Both during MP as well as during reperfusion samples were taken for assessment of liver damage, samples for assessment of liver function were taken during reperfusion.

Preservation Solutions

The UW solution for CS was obtained from DuPont (Viaspan, pH 7.4, 320 mOsmol/kg, Bristol-Myers Squibb, New York, USA). The UW-G solution for MP was prepared according to Belzer's prescription (pH 7.4, 330 mOsmol/kg) (26). Our MP preservation solution Polysol was developed at the Surgical Laboratory of the Academic Medical Center (Amsterdam, The Netherlands) (pH 7.4, 330 mOsmol/kg).

UW-G, Polysol-2 and Krebs-Henseleit buffer (KHB) were all prepared in our laboratory using analytical reagent grade (or better) chemicals from Sigma-Aldrich (Zwijndrecht, The Netherlands), Merck (Haarlem, The Netherlands), Cambrex (Verviers, Belgium), Centrafarm (Etten-Leur, The Netherlands) and Novo Nordisk (Alphen aan den Rijn, The Netherlands). The HES was obtained from Fresenius (Taunusstein, Germany). The solutions were sterilized through a 0.45 µm filter (Dow Corning, Allesley, United Kingdom) and a 0.22 µm filter (Millipack 60, Millipore, Amsterdam, The Netherlands).

Surgical Procedure

Rats were anesthetized with $O_2$/air/Isoflurane (1 L/min:1 L/min:3%). After median laparotomy followed by bilateral subcostal incisions, the animal was heparinized via the caval vein with 0.1 ml heparin (5000 IU/ml, Leo Pharma, Malmö, Denmark). After two min, a phrenotomy was performed to sacrifice the animal. After cessation of blood flow to the liver, the warm ischemic time (WIT) commenced. During WIT the liver was mobilized and the bile duct was cannulated with a 0.9 mm venous catheter (B-Braun, Melsungen, Germany). After 30 min WIT, the liver was washed out with 50 ml of Ringer Lactate (37° C., 8 mmHG) via a portal vein cannula (2.7 mm, enteral feeding tube, Vygon, Valkenswaard, The Netherlands). During washout congestion of the liver was prevented by cutting the infrahepatic caval vein. The suprahepatic caval vein was then cannulated with a 2 mm cannula (Vygon), the infrahepatic caval vein was ligated and after trimming of surrounding tissue the liver was removed and weighed.

Machine Perfusion System

Our machine perfusion system was developed by the Medical Technology Department of the Academic Medical Center (Amsterdam, The Netherlands). Before connecting the liver, the circuit was rinsed with sterile Aquadest and preservation solution. The pressure driven system (15 mmHg) consists of a reservoir containing 350 ml of sterile MP solution (4° C.). After connection of the liver the first 100 ml of solution was allowed to run off freely, without re-entering the system. The remaining 250 ml of solution was recirculated by a roller pump (Ismatec, Glattbrugg, Switzerland). The solution was oxygenated by a glass oxygenator, delivering more than 700 mmHg of oxygen pressure to the organ. Air emboli were removed from the system by a bubble trap, after which the solution was cooled to 4° C. by a heat exchanger (HMT-200, Heto, Breda, The Netherlands). The solution passed a flow meter (HT-207, Transonic Systems Inc, Maastricht, The Netherlands) and then entered the liver via the portal vein cannula. The solution ran back freely from the suprahepatic caval vein cannula into the reservoir.

Normothermic Reperfusion

Reperfusion with Krebs-Henseleit buffer (KHB) was performed after a 30 min rewarming period, to mimic the implantation of the liver into the recipient. Directly prior to reperfusion ammonium chloride was added for function testing.

Reperfusion was performed in the same set-up as MP, except that the reservoir was filled with 350 ml KHB and the temperature was adjusted to 37° C. Before connection of the liver the system was rinsed with sterile Aquadest and KHB. After connection of the liver, again the first 100 ml was allowed to run off freely, without re-entering the circuit. This solution was heated by the heat exchanger and passed through the flow meter and men entered the liver via the portal vein cannula. Samples for assessment of liver damage and liver function were collected posthepatically. Liver temperature was measured with a temperature probe positioned under the liver (Laméris, Nieuwegein, The Netherlands).

The system was cleaned before and after each procedure with alcohol (70%) and sterile water (Aquadest).

Sample Preparation

Perfusate samples for the assessment of hepatocellular injury and liver function were taken during MP and reperfusion. During MP the samples were taken every hour at $t=0$, $t=1$, $t=2$, $t=22$, $t=23$ and $t=24$ h. In the reperfusion phase the samples were taken with 15 min intervals for a period of 60 min.

At the end of the reperfusion phase, liver samples for adenosine tri-phosphate (ATP) assessment were taken from the accessory liver lobe using a freeze clamp for immediate tissue freezing. Liver biopsies were further obtained from the caudate and right liver lobes and were processed in formalin (10% in phosphate buffered saline), liver samples for transmission electron microscopy were obtained from the median lobe and stored to McDowells solution. Finally, liver samples were taken from the left lobe for dry/wet weight analysis.

Liver Damage and Liver Function Studies

Damage parameters; liver damage was assessed by spectrophotometric analysis of aspartate aminotransferase (AST) and alanine aminotransferase (ALT) (27). Perfusate flow was measured during MP and reperfusion in order to assess microvascular integrity.

Function parameters: liver function was assessed by measuring bile production, oxygen consumption, ammonia clearance, urea production and ATP-restoration.

For measurement of bile production, bile was collected during reperfusion via the bile duct cannula. Oxygen consumption was determined by the difference in oxygen concentration (µMol/L) in pre- and posthepatic blood gas samples (ABL, Radiometer, Zoetermeer, The Netherlands), related to perfusate flow and liver wet weight. To measure ammonia clearance and urea production the liver was challenged with 5 mM ammonium chloride (Sigma-Aldrich, Zwijndrecht, The Netherlands). Samples were taken at $t=-5$, $t=0$, $t=15$, $t=30$, $t=45$ and $t=60$ min of reperfusion. To analyse ammonia clearance the samples were processed on ice after dilution (10×) with phosphate buffered saline and acidification with HCl (final concentration: 0.45% m/v). An enzymatic method based on the reaction between ammonia, ketoglutarate and NADPH, catalyzed by glutamate dehydrogenase, was used (28). Urea production was analysed with a colorimetric method, based on its reaction with diacetylmonoxime (Sigma-Aldrich) (29). ATP was measured in freeze-clamped biopsies, which, after pulverization under liquid nitrogen, were extracted with ice cold $HClO_4$ (final concentration: 3.5% m/v). The precipitated protein was removed by rapid centrifugation at 4° C. in a microcentrifuge and the supernatants were neutralized to pH 7 with a mixture of 2 M KOH plus 0.3 M MOPS. ATP was measured fluorimetrically using glucose, $NADP^+$, glucose 6-phosphate dehydrogenase and hexokinase (30).

Histology

Liver biopsies for histology were stored in formalin (10% in phosphate buffered saline), paraffinized and cut in 4 µm sections. After Hematoxylin and Eosin staining, the sections were evaluated with light microscopy using a 9-point semi-quantitative damage score, modified by Tojimbara and Martin (31,32).

Biopsies from the left lateral lobe were taken for assessment of dry/wet weight ratios: livers were weighed immediately after reperfusion. Thereafter, these biopsies were kept in a climate chamber at 60° C. Biopsies were weighed every 3-5 days, until decrease in weight was no longer seen. To measure the dry/wet weight ratio, the following formula was used: 100%×(1−(dry weight/wet weight)).

Liver biopsies (1 $mm^3$) for Transmission Electron Microscopy (TEM), for ultrastructural investigation, were fixed in McDowells fixative for at least 48 h. Thereafter they were rinsed in Na-phosphate buffer (0.1 M, pH 7.4), postfixed in 1% $OsO_4$, rinsed in water and dehydrated in graded ethanol (70-80-90-96-100%) and propylene oxide. Finally, the specimen were embedded in epon. Ultrathin sections (80 nm) were cut with a Reichert Ultracut E and contrasted with uranyl acetate and lead citrate. Sections were studied with a Philips EM420 operated at 100 kV; images were acquired with a SIS Megaview II camera.

Statistical Analysis

All groups were compared using the Kruskall-Wallis test. In case of significant outcome, differences between individual groups were evaluated by the non-parametric Mann Whitney-U test. For the ammonia clearance and urea production rate an analysis for repeated measurements was used, with a post-hoc test according to Bonferroni. Results in text and graphs are shown as mean±SEM. Statistical significance was defined as $p<0.05$.

Results

General

Mean rat weight and liver weight were 289±7 g and 14.8±0.3 g, respectively (n=18).

Hepatocellular Damage and Perfusate Flow During MP (4° C.)

During MP the release of AST was significantly higher using UW-G, as compared to Polysol, at t=0, t=1, t=2 and t=22 h. ALT release was significantly higher using UW-G as compared to Polysol at all time points (FIG. 1A,B).

Perfusate flow during MP decreased in the MP-UW-G group, resulting in a lower flow at t=22, t=23 and t=24 h as compared to MP-Polysol ($p=0.01$) (FIG. 2A).

Hepatocellular Damage and Perfusate Flow During Reperfusion (37° C.)

AST release (FIG. 3A) was lower after MP-UW-G as compared to CS, on t=30 and t=45 min ($p<0.05$). Using Polysol this release was lower at all time points ($p<0.005$). ALT release showed the same trend (FIG. 3B), but significance was only reached at t=60 min for MP-Polysol as compared to CS (9.7±2.4 versus 47.2±14.2 IU/L, $p<0.05$).

Perfusate flow during reperfusion was significantly higher with MP-Polysol as compared to CS on t=45 and t=60 min and to MP-UW-G at all time points (FIG. 2B). Also perfusate flow was better in the CS group as compared to MP-UW-G at all time points ($p<0.05$).

Hepatocellular Function During Reperfusion (37° C.)

Bile production was highest after MP using Polysol as compared to CS with UW and MP using UW-G (390±23 versus 34±19 and 153±55 μl/h respectively, $p<0.01$). No significant differences were seen between CS-UW and MP-UW-G (Table 1). Oxygen consumption was highest after MP using Polysol, in comparison to MP using UW-G at all time points and in comparison to CS with UW at t=60 (FIG. 4). Ammonia clearance was highest after MP using Polysol and was significantly better than using UW-G at t=15, t=45 and t=60 min and than CS at t=15 min. Urea production was significantly higher in the Polysol groups as compared to UW-G at all time points. There were no differences between Polysol and CS, however, more urea was produced in the CS group as compared to UW-G at t=45 min (FIG. 5A,B).

ATP-Content

ATP-content at the end of the reperfusion phase was significantly higher after MP using Polysol, as compared to both CS in UW and MP using UW-G (7.5±0.6 versus 4.0±0.8 and 2.5±0.6 μMol/g dry weight, respectively).

Histology

Semi-quantitative assessment of damage in hematoxylin and eosin stained sections resulted in a mean score of 2.2±0.2 for livers preserved using Polysol. This was a significantly better score when compared to both CS and MP using UW-G (3.7±0.3 and 4.4±0.3 respectively).

Dry/Wet Weight Ratio

Biopsies taken after reperfusion showed significantly lower dry/wet weight ratios, and therefore less tissue edema, after preservation by MP using Polysol, as compared to CS in UW and MP using UW-G (72.6±0.8 versus 77.1±1.1 and 75.2±0.9%, respectively).

In conclusion, 24 h machine perfusion preservation of the NHBD rat liver using tire newly developed preservation solution Polysol results in less liver damage and better liver function as compared to cold storage in UW and machine perfusion using UW-G. In this example polysol-2 formulation was used, as defined in example 1.

Example 6

Liver transplantation is the treatment of choice in patients with end-stage liver disease (33,34). The quality of the liver graft depends amongst other factors, on the preservation method and the length of the preservation period, i.e. the cold ischemic time. The current gold standard in liver preservation (35) is wash-out of the liver using an appropriate preservation solution, followed by cold storage (CS), enabling human liver allografts to be safely preserved for a period of up to 16 h (36). In this setting, the liver is implanted in the recipient after the preservation phase without any objective knowledge on graft viability. Reliable methods for prior assessment of hepatocellular damage and liver function are lacking in the statically cold stored organ. Donor history, macroscopic evaluation and liver biopsy analysis can merely give an indication of the viability of the cold stored liver graft (37).

The limits of CS in the preservation of most abdominal organs have been reached. As an alternative, machine perfusion preservation (MP) of the liver has come into focus again in experimental studies. MP was already applied in the early sixties (38-40). After wash-out to clear blood remnants, the liver is connected to a recirculating machine perfusion system in which it is perfused with a hypothermic preservation solution for the duration of transport. Several advantages of MP have been postulated over CS: 1) continuous supply of oxygen and nutrients, 2) removal of end-products of metabolism, 3) assessment of liver viability during preservation (41) and 4) potential resuscitation of ischemically damaged organs such as non-heart-beating donor (NHBD) organs (42).

Experimental studies have shown superior results in post-transplant function of liver grafts after MP as compared to CS (43-45). These results can be explained by the fact that although the organ is cooled to 4° C., 7-35% of the intrinsic metabolism is maintained (45). This metabolism, although reduced, could benefit from energy substrates and oxygen, which can only be provided by continuous oxygenated MP. The modified University of Wisconsin solution (UW-Gluconate: UW-G), most often used in experimental MP, lacks substrates for energy, carbohydrate and fat metabolism of the liver (47-51). Although literature on the role of nutrients in solutions for hypothermic organ preservation is scarce (52-54), we hypothesize that a perfusion solution enriched with nutrients results in better quality liver preservation. This led to the development of a new preservation solution, Polysol, which contains the required nutrients for liver metabolism along with potent buffers and free radical scavengers. The components which amongst others make the difference between Polysol and other MP preservation solutions are amino acids, such as glutamine, histidine, tryptophan and arginine, and vitamins, such as ascorbic acid and alpha-tocopherol.

The aim of this study was to assess MP of rat livers using Polysol and to compare results with MP using UW-G, both in relation to the gold standard CS method using UW. To this end, both preservation methods and MP solutions were assessed in the isolated perfused rat liver model (IPRL).

Materials and Methods

Animals and Surgery

Male Wistar rats (Harlan, Horst, The Netherlands), weighing 350 g (+/−50 g) were used as liver donor. The animals were housed under standardized conditions with a 12/12 h dark/light cycle and ad libitum access to water and a standard pellet chow (Hope Farms, Woerden, The Netherlands), until directly prior to the experiment. All animals were handled in accordance to Dutch regulations and principles of animal care, under approval of the Animal Ethical Committee of the University of Amsterdam.

Rats were anesthetized with $O_2$/air/Isoflurane (1 L/min:1 L/min:3%) and an intraperitoneal injection of 0.1 ml/100 g body weight FFM (Hypnorm/Dormicum/aquadest: 1:1:2). During surgery, anesthesia was maintained with inhalation of $O_2$/air/Isoflurane through a mask.

After median laparotomy followed by bilateral subcostal incisions, the liver was mobilized and the bile duct cannulated with a 0.9 mm catheter (B-Braun, Melsungen, Germany). Before cannulation of the portal vein, the animal was heparinized via the caval vein with 0.1 ml Heparin (5000 IU/ml, Leo Pharma, Malmö, Denmark). The liver was washed out with 50 ml of Ringer Lactate (37° C., 10 cm $H_2O$, Baxter, Utrecht, The Netherlands) via the portal vein cannula (0.8 fr, enteral feeding tube, Vygon, Valkenswaard, The Netherlands). During wash-out, the animal was bled via incision of the abdominal caval vein. The suprahepatic caval vein was cannulated with a 0.6 fr cannula (Vygon), the infrahepatic caval vein ligated and after trimming of surrounding tissue the liver was excised and weighed.

Machine Perfusion System

A dual machine perfusion system was developed by the Medical Technical Development Department of the Academic Medical Center (AMC, Amsterdam, The Netherlands) enabling both MP and reperfusion (RP) phase in a single set-up (Addendum 2). Prior to connection of the excised liver, the circuit was rinsed with 200 ml of sterile Aquadest and subsequently with 50 ml of preservation solution. The pressure controlled perfusion system consists of a reservoir containing 350 ml of sterile MP solution. After connecting the liver to the system, the first 100 ml of perfusion solution was collected. The remaining 250 ml of solution was recirculated by a roller pump (Ismatec, Glattbrugg, Switzerland). The perfusion solution was oxygenated with carbogen (95% $O_2$/5% $CO_2$, 1 L/min, Hoekloos Medical, Amsterdam, The Netherlands) by a glass oxygenator, resulting in a prehepatic oxygen tension of approximately 700 mmHg. Air emboli were removed from the system by a bubble trap, after which the solution was cooled using a heat exchanger (HMT-200, Heto, Breda, The Netherlands). The perfusion solution passed through an in-line flow meter (HT-207, Transonic Systems Inc, Maastricht, The Netherlands), entered the liver through the portal vein cannula and ran freely via the suprahepatic caval vein cannula into the reservoir.

Reperfusion was performed along the same circuit as described above, with a second reservoir now containing 400 ml of Krebs-Henseleit buffer (KHB) solution at 37° C. Before re-connecting the liver, the system was rinsed with 200 ml sterile Aquadest and 50 ml KHB. After re-connection of the liver, the first 100 ml was drained to prevent it from re-entering the circuit. The remaining 250 ml of perfusate was oxygenated with carbogen. Samples were obtained from the tubing directly pre- or posthepatically. Temperature was recorded by a probe (Laméris, Nieuwegein, The Netherlands) placed under the liver. After each procedure, the circuit was rinsed and steam-sterilized (134° C. for 16 min).

Experimental Groups and Preservation Conditions

This study comprised of 3 experimental groups: 1) CS-UW (N=5); 2) MP-UW-G (N=5) and 3) MP-Polysol (N=5). The isolated livers were preserved by either CS or MP for 24 h and thereafter reperfused.

After wash-out with RL (4° C.), the liver was flushed in situ with the preservation solution. CS livers were flushed with 50 ml UW (4° C.), placed in a sterile cup containing 100 ml of UW and stored on melting ice in a cold chamber (4° C.) for 24 h. MP livers were connected to the perfusion system via the portal vein directly after wash-out and harvesting, flushed with 100 ml of either UW-G or Polysol and continuously perfused with this solution at 4° C. for 24 h. After the preservation period, all livers were reperfused for 60 min at 37° C. with oxygenated KHB.

Preservation Solutions:

For cold storage, the University of Wisconsin preservation solution (Viaspan, Bristol-Myers Squibb, New York, USA) was used. The UW-G solution for MP was prepared according to Belzer's prescription (pH 7.4 at 4° C., 330 mosmol/kg) (55). The MP preservation solution Polysol (pH 7.4 at 4° C., 330 mosmol/kg) was developed at the Surgical Laboratory of the AMC. For reperfusion, Krebs-Henseleit Buffer (KHB), without bovine serum albumin (pH 7.4 at 37° C., 320 mosmol/kg) was used. UW-G, Polysol and KHB were all prepared in our laboratory using analytical reagent grade (or better) chemicals from Sigma-Aldrich (Zwijndrecht, The Netherlands), Merck (Haarlem, The Netherlands), Cambrex (Verviers, Belgium), Centrafarm (Etten-Leur, The Netherlands) and Novo Nordisk (Alphen aan den Rijn, The Netherlands). The Hydroxyethylstarch (HES) was obtained from Fresenius (Taunusstein, Germany). Prior to use, the solutions were sterilized by filtration through a 0.45 μm ampul filter (DowCorning, Allesley, United Kingdom) and a 0.22 μm filter (Millipack 60, Millipore, Amsterdam, The Netherlands).

Assessment of Hepatocellular Damage and Liver Function:

Samples for hepatocellular damage assessment were taken every 10 min during 60 min of RP.

Liver damage was assessed by direct analysis of aspartate aminotransferase (AST), alanine aminotransferase (ALT) and lactate dehydrogenase (LDH) in posthepatic perfusate samples (Laboratory of Clinical Chemistry, AMC, The Netherlands) (56). Alpha-GST (alpha-glutathione-S-transferase) levels were determined using a rat alpha-GST ELISA kit (Biotrin, Dublin, Ireland).

Liver function was assessed by monitoring bile production during 60 min of RP. Furthermore, lactate production (Laboratory of Clinical Chemistry, AMC, The Netherlands) and perfusate pH (ABL, Radiometer, Zoetermeer, The Netherlands) were measured during reperfusion.

Histology and Dry/Wet Weight Ratio:

At the end of the RP phase biopsies were taken from the caudate and right lateral lobes. Biopsies were stored in formaldehyde (10%) and embedded in paraffin.

Paraffin sections (4 μm) were stained with hematoxylin and eosin (H&E) and evaluated with light microscopy. A 9-point scale was used for morphological classification of hepatic injury graded on a scale of 1 (excellent) to 9 (poor) (57,58): 1. normal rectangular structure, 2. rounded hepatocytes with an increase of sinusoidal spaces, 3. vacuolization in zone 3, 4. vacuolization in zone 2, 5. vacuolization in zone 1, 6. vacuolization and nuclear pyknosis in zone 3, 7. vacuolization and nuclear pyknosis in zone 2, 8. vacuolization and nuclear pyknosis in zone 1 and 9. necrosis.

For dry/wet weight ratio's liver biopsies were weighed immediately after reperfusion and were thereafter stored in a 60° C. stove. Biopsies were weighed again every 7 days, until reduction of liver weight had stopped. To demonstrate the amount of liver edema, the following calculation was used 1−(dry weight/wet weight)×100%.

Statistical Analysis:

The Kruskal-Wallis test was used for overall comparison of the three groups. If significant differences were shown, differences between individual groups were evaluated by the non-parametric Mann Whitney test. Results in text and graphs are shown as mean±SEM. Statistical significance was defined as p<0.05.

Results

Perfusion Parameters:

Liver weights did not differ significantly between experimental groups (16.5±0.5 g). During both hypothermic MP and normothermic RP the perfusion pressure was constantly kept at 20 cm $H_2O$ (gravity controlled). The perfusion flow during hypothermic MP reached 1 ml/min/gram liver maximally. During normothermic RP a maximum flow of 3 ml/min/g liver was recorded. Oxygenation during hypothermic MP resulted in a perfusate $pO_2$ of approximately 700 mmHg and during normothermic RP, due to the higher temperature, in a $pO_2$ of approximately 500 mmHg. The temperature recorded during normothermic RP was 37.1±0.4° C.

Hepatocellular Damage:

ALT release after 24 h cold ischemic time was significantly higher after CS with UW as compared to MP using UW-G at t=0 min (4.6±2.4 versus 0.4±0.2 IU/L) and t=10 min (5.4±1.7 versus 1.4±0.2 IU/L) (FIG. 1A). However, when CS-UW is compared to MP-Polysol, ALT levels are significantly lower after MP-Polysol at all time points except t=0 min and t=50 min. LDH levels appear higher after 24 h CS-UW, without reaching significancy. LDH is significantly higher after CS-UW at t=10 min (FIG. 1B) as compared to MP using either UW-G or Polysol Perfusate flow, pH and lactate production were not significantly different (data not shown).

When comparing the two MP solutions, less damage after 24 h of MP-Polysol was seen, as shown by the lower AST levels (FIG. 1C). Although there was a trend in favor of Polysol at all time points, there were no significant differences in ALT (FIG. 1A), LDH (FIG. 1B), perfusate flow, pH and lactate production (data not shown). Release of α-GST (FIG. 2) at t=40 min was lower after MP-Polysol as compared to CS-UW (125.5±10.5 versus 46.4±9.1, respectively, p<0.02) and to MP-UW-G (101.6±12.0 versus 46.4±9.1, respectively, p<0.02).

Hepatocellular Function:

Bile production appeared higher after MP-Polysol than after MP-UW-G or CS-UW (355±82.3 versus 256±26.2 and 180±61.99 µl/h, respectively). However, this did not reach significancy (FIG. 3).

Histology:

After histopathological scoring of the liver sections, a better median score was assigned to the MP groups using UW-G and Polysol (2.0±0.6 and 1.6±0.4 points respectively) as compared to the CS-UW livers (4.5±0.9 points) (p=0.06 for UW-G and p=0.03 for Polysol). There were no significant differences between the MP groups (FIG. 4).

The dry/wet weight ratio of liver sections was highest in the MP groups, accounting for the lowest percentage of edema (FIG. 5). Percentages were 76±1.0 versus 72±0.5 versus 72±0.7 respectively.

In conclusion, preservation of the heart-beating donor rat liver by machine perfusion results in better quality liver preservation as compared to cold storage. Machine perfusion using the new, enriched preservation solution, Polysol-2, results in equal to better quality liver preservation when compared to UW-G. In this example polysol-2 formulation as defined in example 1 was used, and polysol refers to polysol-2.

REFERENCE LIST

1. Kim J S, Boudjema K, D'Alessandro A, Southard J H. Machine perfusion of the liver: maintenance of mitochondrial function after 48-hour preservation. Transplant Proc 1997:29: 3452-3454.
2. Pienaar B H, Lindell S L, Van Gulik T, Southard J H, Belzer F O. Seventy-two-hour preservation of the canine liver by machine perfusion. Transplantation 1990:49: 258-260.
3. Southard J H, Lindell S, Ametani M, Richer J P, Vos A W. Kupffer cell activation in liver preservation: cold storage vs machine perfusion. Transplant Proc 2000:32: 27-28.
4. Kim J S, Boudjema K, D'Alessandro A, Southard J H. Machine perfusion of the liver: maintenance of mitochondrial function after 48-hour preservation. Transplant Proc 1997:29: 3452-3454.
5. Southard J H, Lindell S, Ametani M, Richer J P, Vos A W. Kupffer cell activation in liver preservation: cold storage vs machine perfusion. Transplant Proc 2000:32: 27-28.
6. Xu H, Lee C Y, Clemens M G, Zhang J X. Pronlonged hypothermic machine perfusion preserves hepatocellular function but potentiates endothelial cell dysfunction in rat livers. Transplantation 2004:77: 1676-1682.
7. Bergmeyer H U. Standardization of enzyme assays. Clin Chem 1972:18: 1305-1311.
8. Fonseca-Wollheim F. [Direct determination of plasma ammonia without deproteinization. An improved enzymic determination of ammonia, II (author's transl)]. Z Klin Chem Klin Biochem 1973:11: 426-431.
9. Crocker C L. Rapid determination of urea nitrogen in serum or plasma without deproteinization. Am J Med Technol 1967:33: 361-365.
10. United Network for Organ Sharing. Lancet 2003:340: 1373-1376.
11. Gridelli B, Spada M, Petz W et al. Split-liver transplantation eliminates the need for living-donor liver transplantation in children with end-stage cholestatic liver disease. Transplantation 2003:75: 1197-1203.
12. Neuberger J M, Lucey M R. Living-related liver donation: the inevitable donor deaths highlighted the need for greater transparency. Transplantation 2004:77: 489-490.
13. Nunez A, Goodpastor S E, Goss J A, Washburn W K, Halff G A. Enlargement of the cadaveric-liver donor pool using in-situ split-liver transplantation despite complex hepatic arterial anatomy. Transplantation 2003:76: 1134-1136.
14. Otte J B. Donor complications and outcomes in live-liver transplantation. Transplantation 2003:75: 1625-1626.
15. Fukumori T, Kato T, Levi D et al. Use of older controlled non-heart-beating donors for liver transplantation. Transplantation 2003:75: 1171-1174.
16. Oh C K, Sanfey H A, Pelletier S J, Sawyer R G, McCullough C S, Pruett T L. Implication of advanced donor age on the outcome of liver transplantation. Clin Transplant 2000:14: 386-390.
17. Verran D, Kusyk T, Painter D et al. Clinical experience gained from the use of 120 steatotic donor livers for orthotopic liver transplantation. Liver Transpl 2003:9: 500-505.
18. Kim J S, Boudjema K, D'Alessandro A, Southard J H. Machine perfusion of the liver: maintenance of mitochondrial function after 48-hour preservation. Transplant Proc 1997:29: 3452-3454.

19. Southard J H, Lindell S, Ametani M, Richer J P, Vos A W. Kupffer cell activation in liver preservation: cold storage vs machine perfusion. Transplant Proc 2000:32: 27-28.
20. Xu H, Lee C Y, Clemens M G, Zhang J X. Pronlonged hypothermic machine perfusion preserves hepatocellular function but potentiates endothelial cell dysfunction in rat livers. Transplantation 2004:77: 1676-1682.
21. Marsh D C, Lindell S L, Fox L E, Belzer F O, Southard J H. Hypothermic preservation of hepatocytes. I. Role of cell swelling. Cryobiology 1989:26: 524-534.
22. Pienaar B H, Lindell S L, Van Gulik T, Southard J H, Belzer F O. Seventy-two-hour preservation of the canine liver by machine perfusion. Transplantation 1990:49: 258-260.
23. Morariu A M, Vd P A, Oeveren V et al. Hyperaggregating effect of hydroxyethyl starch components and University of Wisconsin solution on human red blood cells: a risk of impaired graft perfusion in organ procurement? Transplantation 2003:76: 37-43.
24. Rubinsky B. Principles of low temperature cell preservation. Heart Fail Rev 2003:8: 277-284.
25. Bessems M, Doorschodt B M, van Vliet A. K., Van Gulik T. Improved rat liver preservation by hypothermic continuous machine perfusion using Polysol, a new, enriched preservation solution. Liver Transpl 2005:11: 539-546.
26. Pienaar B H, Lindell S L, Van Gulik T, Southard J H, Belzer F O. Seventy-two-hour preservation of the canine liver by machine perfusion. Transplantation 1990:49: 258-260.
27. Bergmeyer H U. Standardization of enzyme assays. Clin Chem 1972:18: 1305-1311.
28. Fonseca-Wollheim F. [Direct determination of plasma ammonia without deproteinization. An improved enzymic determination of ammonia, II (author's transl)]. Z Klin Chem Klin Biochem 1973:11: 426-431.
29. Crocker C L. Rapid determination of urea nitrogen in serum or plasma without deproteinization. Am J Med Technol 1967:33: 361-365.
30. Williamson J R, Corkey B E. Assay of citric acid cycle intermediates and related compounds—update with tissue metabolite levels and intracellular distribution. Methods Enzymol 1979:55: 200-222.
31. Martin H, Bournique B, Sarsat J P, Albaladejo V, Lerche-Langrand C. Cryopreserved rat liver slices: a critical evaluation of cell viability, histological integrity, and drug-metabolizing enzymes. Cryobiology 2000:41: 135-144.
32. Tojimbara T, Wicomb W N, Garcia-Kennedy R et al. Liver transplantation from non-heart beating donors in rats: influence of viscosity and temperature of initial flushing solutions on graft function. Liver Transpl Surg 1997:3: 39-45.
33. Neuhaus P, Bechstein W O, Hopf U, Blumhardt G, Steffen R. [Indications and current developments in liver transplantation]. Leber Magen Darm 1989:19: 289-308.
34. Ringe B. Quadrennial review on liver transplantation. Am J Gastroenterol 1994:89: S18-S26.
35. St Peter S D, Imber C J, Friend P J. Liver and kidney preservation by perfusion. Lancet 2002:359: 604-613.
36. Porte R J, Ploeg R J, Hansen B et al. Long-term graft survival after liver transplantation in the UW era: late effects of cold ischemia and primary dysfunction. European Multicentre Study Group. Transpl Int 1998:11 Suppl 1: S164-S167.
37. St Peter S D, Imber C J, Friend P J. Liver and kidney preservation by perfusion. Lancet 2002:359: 604-613.
38. Lee D, Walker J M. Maintenance of the functional state of isolated rat liver by hypothermic perfusion with an erythrocyte-free medium. Transplantation 1977:23: 136-141.
39. Turner M D, Alican F. Successful 20-hour storage of the canine liver by continuous hypothermic perfusion. Cryobiology 1970:6: 293-301.
40. St Peter S D, Imber C J, Friend P J. Liver and kidney preservation by perfusion. Lancet 2002:359: 604-613.
41. Adham M, Peyrol S, Chevallier M et al. The isolated perfused porcine liver: assessment of viability during and after six hours of perfusion. Transpl Int 1997:10: 299-311.
42. Schon M R, Hunt C J, Pegg D E, Wight D G. The possibility of resuscitating livers after warm ischemic injury. Transplantation 1993:56: 24-31.
43. Compagnon P, Clement B, Campion J P, Boudjema K. Effects of hypothermic machine perfusion on rat liver function depending on the route of perfusion. Transplantation 2001:72: 606-614.
44. Kim J S, Boudjema K, D'Alessandro A, Southard J H. Machine perfusion of the liver: maintenance of mitochondrial function after 48-hour preservation. Transplant Proc 1997:29: 3452-3454.
45. Pienaar B H, Lindell S L, Van Gulik T, Southard J H, Belzer FO. Seventy-two-hour preservation of the canine liver by machine perfusion. Transplantation 1990:49: 258-260.
46. Rubinsky B. Principles of low temperature cell preservation. Heart Fail Rev 2003:8: 277-284.
47. Boudjema K, Lindell S L, Belzer F O, Southard J H. Effects of method of preservation on functions of livers from fed and fasted rabbits. Cryobiology 1991:28: 227-236.
48. Kim J S, Boudjema K, D'Alessandro A, Southard J H. Machine perfusion of the liver: maintenance of mitochondrial function after 48-hour preservation. Transplant Proc 1997:29: 3452-3454.
49. Pienaar B H, Lindell S L, Van Gulik T, Southard J H, Belzer F O. Seventy-two-hour preservation of the canine liver by machine perfusion. Transplantation 1990:49: 258-260.
50. Southard J H, Lindell S, Ametani M, Richer J P, Vos A W. Kupffer cell activation in liver preservation: cold storage vs machine perfusion. Transplant Proc 2000:32: 27-28.
51. Uchiyama M, Matsuno N, Nakamura Y et al. Usefulness of preservation by machine perfusion of liver grafts from non-heart-beating donors—a porcine model. Transplant Proc 2003:35: 105-106.
52. Marsh D C, Belzer F O, Southard J H. Hypothermic preservation of hepatocytes. II. Importance of Ca2 and amino acids. Cryobiology 1990:27: 1-8.
53. Charrueau C, Blonde-Cynober F, Coudray-Lucas C et al Prevention of proteolysis in cold-stored rat liver by addition of amino acids to the preservation solution. J Gastroenterol Hepatol 2000:15: 1199-1204.
54. Churchill T A, Green C J, Fuller B J. Protective properties of amino acids in liver preservation: effects of glycine and a combination of amino acids on anaerobic metabolism and energetics. J Hepatol 1995:23: 720-726.
55. Pienaar B H, Lindell S L, Van Gulik T, Southard J H, Belzer F O. Seventy-two-hour preservation of the canine liver by machine perfusion. Transplantation 1990:49: 258-260.
56. Bergmeyer H U. Standardization of enzyme assays. Clin Chem 1972:18: 1305-1311.
57. Martin H, Bournique B, Sarsat J P, Albaladejo V, Lerche-Langrand C. Cryopreserved rat liver slices: a critical evalu- 58. Tojimbara T, Wicomb W N, Garcia-Kennedy R et al. Liver transplantation from non-heart beating donors in rats: influence of viscosity and temperature of initial flushing solutions on graft function. Liver Transpl Surg 1997:3: 39-45.

The invention claimed is:

1. A machine perfusion solution for maintaining donor organ viability consisting of a mammalian tissue culture medium selected from the group consisting of Minimal Essential Medium Eagle (MEM), Dulbecco's Modified Eagle Media (DMEM), RPMI 1640 Media, DMEM/F-12 Media, Hams F-10, Hams F12, Iscove's Modified Dulbecco's Medium, Leibovitz's L-15 Media, Minimum Essential media with Earle's Salts, and Williams medium E, wherein the tissue culture medium is modified to:
   (a) 10 to 50 g/L polyethylene glycol (PEG) having a molecular weight of 25 to 50 kDa
   (b) 1,000 to 10,000 mg/L HEPES;
   (c) 1,000 to 5,000 mg/L of each of raffinose and trehalose;
   (d) 1,000 to 5,000 mg/L of gluconic acid;
   (e) 0.7 to 1.8 g/L glutathione;
   (f) 0.00001 to 0.001 g/L vitamin E;
   (g) 0.01 to 0.1 g/L of ascorbic acid; and
   (h) 0.00001 to 0.001 g/L selenium;
   wherein the solution has:
      (i) a buffer capacity of at least a Beta of 20,
      (ii) a [$Na^+$] concentration of less than 140 mM, and a [$K^+$] concentration of less than 25 mM, wherein the ratio of [$Na^+$] to [$K^+$] is at least 5:1,
      (iii) a pH between 7 and 7.8,
      (iv) an osmolarity between 300 and 350, and
      (v) an oncotic pressure between 20 and 30 mmHg.

2. The solution according to claim 1, having a physiological oncotic pressure of 25 mmHg.

3. The solution according to claim 1, having a physiological osmolarity of 330 mOsm.

4. The solution according to claim 1, wherein the tissue culture medium being modified is Williams Medium E.

5. The solution according to claim 4, the concentration of at least one amino acid found in Williams medium E is 2 to 10 fold greater than that of medium E.

6. The solution according to claim 5 wherein the amino acid is arginine, asparagine, cystine, histidine, glutamine, methionine, phenylalanine, proline, serine or tryptophan.

7. The solution according to claim 1, wherein the source of selenium is $NaSeO_3.5H_2O$.

8. The solution according to claim 1, comprising PEG having a molecular weight of 30,000 dalton.

9. The solution according to claim 1, having PEG in a concentration of 20 to 50 g/L.

10. The solution according to claim 1, wherein the [$Na^+$] concentration is less than 120 mM.

11. The solution according to claim 1, comprising quantities of glucose, amino acids and vitamins in quantities sufficient to maintain the metabolic rate at 18° C. at a level of at least 10% of the level at physiological temperatures.

12. A method for preserving an organ comprising placing the organ in a solution according to claim 1.

13. The method according to claim 12 wherein the solution is oxygenated and has a temperature of between 0° C. and 20° C.

14. The method according to claim 13 wherein the solution has a temperature of between 0° C. and 10° C.

15. The method according to claim 12 further comprising rinsing or flushing the organ with the solution.

16. The method according to claim 12 comprising placing the organ under continuous or pulsatile perfusion with the solution.

17. The method according to claim 12 wherein the organ is a heart, lung, pancreas, kidney or liver.

18. The method according to claim 17, wherein the organ is obtained from a non-heart-beating donor.

19. The method according to claim 17, wherein the organ is a human organ.

20. A solution for maintaining donor organ viability having:
   (i) a buffer capacity of at least a Beta of 20,
   (ii) a [$Na^+$] concentration of less than 120 mM, and a [$K^+$] concentration of less than 25 mM, wherein the ratio of [$Na^+$] to [$K^+$] is at least 5:1,
   (iii) a pH between 7 and 7.8,
   (iv) an osmolarity between 300 and 350, and
   (v) an oncotic pressure between 20 and 30 mmHg, and comprising:
      (a) 22.5 to 30 mg/L $CaCl_2$ (anhyd) $CuSO_4.5H_2O$
      (b) 75 to 100 mg/L $MgSO_4$ (anhyd.)
      (c) 75 to 100 mg/L $MgSO_47H_2O$
      (d) 0 to 720 mg/L NaCl
      (e) 900 to 1500 mg/L Glutathione (reduced)
      (f) 187.5 to 250.00 mg/L L-Arginine
      (g) 90 to 120 mg/L L-Asparagine $H_2O$
      (h) 30 to 40 mg/L L-Cysteine
      (i) 45 to 60 mg/L L-Cystine
      (j) 735 to 980 mg/L Histidine
      (k) 45 to 33.75 mg/L L-Methionine
      (l) 50 to 37.5 mg/L L-Phenylalanine
      (m) 67.5 to 90 mg/L L-Proline
      (n) 22.5 to 30 mg/L L-Serine
      (o) 135 to 180 mg/L L-Thryptophan
      (p) 15 to 20 mg/L Ascorbic Acid
      (q) 9 to 12 mg/L i-Inositol
      (r) 0.75 to 1 mg/L Riboflavin
      (s) 7.5 to 10 mg/L Thiamine HCl
      (t) 10 to 100 mg/L ascorbic acid
      (u) 0.01 to 1 mg/L selenium
      (v) 548.91 to 731.88 mg/L $MgCl_26H_2O$
      (w) 1,000 to 10,000 mg/L HEPES
      (x) 1020.67 to 1360.9 mg/L $KH_2PO_4.H_2O$
      (y) 252.75 to 337 L-Ornithine
      (z) 7.5 to 10 ml/L Glutamine
      (aa) 0.375 to 0.5 mg/L Nicotinic Acid
      (ab) 1005 to 1340 mg/L Adenosine
      (ac) 510 to 680 mg/L Adenine
      (ad) 122.4 to 163.2 mg/L Allopurinol
      (ae) 1,000 to 5,000 mg/L raffinose
      (af) 1,000 to 5,000 mg/L trehalose
      (ag) 1,000 to 5,000 mg/L gluconic acid
      (ah) 10,000 to 50,000 mg/L polyethylene glycol (PEG).

* * * * *

UNITED STATES PATENT AND TRADEMARK OFFICE
CERTIFICATE OF CORRECTION

| | | |
|---|---|---|
| PATENT NO. | : 8,637,230 B2 | Page 1 of 1 |
| APPLICATION NO. | : 11/719185 | |
| DATED | : January 28, 2014 | |
| INVENTOR(S) | : Doorschodt et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1348 days.

Signed and Sealed this
Second Day of June, 2015

Michelle K. Lee
*Director of the United States Patent and Trademark Office*